United States Patent
Chorev et al.

(10) Patent No.: US 12,198,810 B2
(45) Date of Patent: Jan. 14, 2025

(54) SYSTEMS AND METHODS FOR SELECTING A THERAPY FOR TREATING A MEDICAL CONDITION OF A PERSON

(71) Applicant: Nucleai Ltd, Tel-Aviv (IL)

(72) Inventors: Lotan Chorev, Kfar Hess (IL); Kira Deborah Nahum Sacks, Ra'anana (IL); Eliron Amir, Kfar-Saba (IL); Ifat Rotbein, Kfar-Saba (IL); Yuval Gabay, Herzliya (IL); Roman Gluskin, Tel-Aviv (IL); Ran Shadmi, Kfar-Saba (IL)

(73) Assignee: Nucleai Ltd, Tel-Aviv (IL)

( * ) Notice: Subject to any disclaimer, the term of this patent is extended or adjusted under 35 U.S.C. 154(b) by 561 days.

(21) Appl. No.: 17/624,398

(22) PCT Filed: Jul. 2, 2020

(86) PCT No.: PCT/IL2020/050738
§ 371 (c)(1),
(2) Date: Jan. 3, 2022

(87) PCT Pub. No.: WO2021/001831
PCT Pub. Date: Jan. 7, 2021

(65) Prior Publication Data
US 2022/0359077 A1    Nov. 10, 2022

Related U.S. Application Data

(60) Provisional application No. 62/869,571, filed on Jul. 2, 2019.

(51) Int. Cl.
| G06K 9/00 | (2022.01) |
| G06T 7/00 | (2017.01) |
| G06T 7/11 | (2017.01) |
| G06V 20/69 | (2022.01) |
| G16H 50/20 | (2018.01) |

(52) U.S. Cl.
CPC .......... G16H 50/20 (2018.01); G06T 7/0012 (2013.01); G06T 7/11 (2017.01); G06V 20/695 (2022.01);
(Continued)

(58) Field of Classification Search
CPC ......... G16H 50/20; G06T 7/11; G06T 7/0012; G06T 2207/20081; G06T 2207/30004; G06V 20/695; G06V 20/698
(Continued)

(56) References Cited

U.S. PATENT DOCUMENTS

2022/0245802 A1*    8/2022    Wang .................... G16H 50/20

FOREIGN PATENT DOCUMENTS

WO    WO 2021/001831    1/2021

OTHER PUBLICATIONS

Zhou, Yanning, et al. "Cgc-net: Cell graph convolutional network for grading of colorectal cancer histology images." Proceedings of the IEEE/CVF international conference on computer vision workshops. 2019. (Year: 2019).*

(Continued)

*Primary Examiner* — Jonathan S Lee

(57) ABSTRACT

A method comprising receiving images depicting stained target tissue, segmenting the images into cell type and region type segmentations, extracting cell phenotype features from an analysis of the stains for cell type segmentations, clustering the cell type segmentations, computing feature vectors each including the respective cell phenotype features, and an indication of a location of the cell type segmentation relative to region type segmentation(s), creating a cell-graph based on the feature vectors of cell type segmentations and/or clusters, wherein each node denotes respective cell type segmentation and/or respective cluster and includes the feature vector, and edges represent a physical distance
(Continued)

between cell type segmentations and/or clusters corresponding to the respective nodes, inputting the cell-graph into a graph neural network, and obtaining an indication of a target therapy likely to be effective for treatment of medical condition in the subject as an outcome of the graph neural network.

20 Claims, 9 Drawing Sheets

(52) U.S. Cl.
CPC .. *G06V 20/698* (2022.01); *G06T 2207/20081* (2013.01); *G06T 2207/30004* (2013.01)

(58) Field of Classification Search
USPC ......................................................... 382/133
See application file for complete search history.

(56) References Cited

OTHER PUBLICATIONS

Rhee, Sungmin. Optimization and Machine Learning Algorithms for Condition-Specific Biological Network Construction and Analyses. Diss., Seoul National University, 2018. (Year: 2018).*

Valenchon, Juliette. Graph-based machine learning algorithms for predicting disease outcomes. McGill University (Canada), 2019. (Year: 2019).*

International Preliminary Report on Patentability Dated Jan. 13, 2022 From the International Bureau of WIPO Re. Application No. PCT/IL2020/050738. (13 Pages).

International Search Report and the Written Opinion Dated Oct. 9, 2020 From the International Searching Authority Re. Application No. PCT/IL2020/050738. (16 Pages).

Bilgin et al. "Cell-Graph Mining for Breast Tissue Modeling and Classification", 2007 29th Annual International Conference of the IEEE Engineering in Medicine and Biology Society, EMBC, XP055530297, Lyon, France, Aug. 22-26, 2007, p. 5311-5314, Aug. 22, 2007.

Yener "Cell-Graphs: Image-Driven Modeling of Structure-Function Relationship", Communications of the ACM, 60(1): 74-84, Dec. 20, 2016.

Zhou et al. "CGC-Net: Cell Graph Convolutional Network for Grading of Colorectal Cancer Histology Images", 2009 IEEE/CVF International Conference on Computer Vision Workshop, ICCVW, XP033732554, Seoul, South Korea, Oct. 27-28, 2019, p. 388-398, Oct. 27, 2019.

Zhou et al. "Graph Neural Networks: a Review of Methods and Applications", ArXiv Preprint ArXiv:1812.08434v1, p. 1-20, Dec. 20, 2018.

* cited by examiner

| Variable (training set) | P-Value | Hazard Ratio (95% CI) |
|---|---|---|
| Age at diagnosis | 0.12 | 1.14 (0.97-1.35) |
| Stage | 0.2 | 2.07 (0.68-6.31) |
| Spatial Recurrence Score | <0.001 | 6.61 (2.51-17.46) |

SYSTEMS AND METHODS FOR SELECTING A THERAPY FOR TREATING A MEDICAL CONDITION OF A PERSON

RELATED APPLICATIONS

This application is a National Phase of PCT Patent Application No. PCT/IL2020/050738 having International filing date of Jul. 2, 2020, which claims the benefit of priority under 35 USC § 119 (e) of U.S. Provisional Patent Application No. 62/869,571 filed on Jul. 2, 2019. The contents of the above applications are all incorporated by reference as if fully set forth herein in their entirety.

BACKGROUND

The present invention, in some embodiments thereof, relates to medical therapies and, more specifically, but not exclusively, to systems and methods for selection of an effective therapy for treating a medical condition in a subject and/or for predicting of clinical prognosis and/or for predicting likelihood of a genetic mutation present in a target tissue.

There may be several possible therapies available for treating a certain medical condition. Selecting the right therapy for the right person plays a key role in treating the person for a medical condition. Some therapies may work for one person, but may not work for another person. For example, immunotherapy is a type of treatment for cancer, in which the immune system is activated or suppressed. Immune cells may be stimulated to target and destroy abnormal tumor cells in the body of the person. Some immunotherapies are very effective for treating of cancer in one person, but not effective for treating the same cancer in another person.

SUMMARY

According to a first aspect, a computer implemented method of at least one of: selecting a therapy for treating a medical condition of a person, predicting prognosis of a medical condition, and predicting genetic mutations of a target tissue, comprises: receiving a plurality of images of at least one slide depicting at least a portion of the target tissue of the person depicting the medical condition stained with a plurality of stains indicative of respective biomarkers, creating a plurality of segmentations, by segmenting for each of the plurality of images, into a plurality of cell type segmentations, and a plurality of region type segmentations, extracting, for each of the cell type segmentations, a plurality of cell phenotype features from an analysis of the plurality of stains, clustering the cell type segmentations according to at least one clustering requirement to create a plurality of clusters, assigning, to at least one of: each respective cell type segmentation and each respective cluster, a feature vector including the cell phenotype features extracted for the respective segmentation, and an indication of a location of the cell type segmentation relative to one or more region type segmentations, creating a cell-graph based on the feature vectors of the plurality of at least one of: cell type segmentations and clusters, wherein each node of the graph denotes at least one of: respective cell type segmentation and respective cluster, each node includes associated corresponding feature vector, and edges of the graph represent a physical distance between the at least one of: cell type segmentations and clusters corresponding to the respective nodes, inputting the cell-graph into a graph neural network trained on a training dataset including, for each of a plurality of sample individuals, a plurality of graphs, an indication of an therapy administered to the respective sample individual and at least one of: a clinical outcome of the respective subject individual treated with the therapy, a prognosis for the respective subject, an indication of at least one certain genetic mutation of the target tissue of the respective subject, and obtaining at least one of: an indication of a target therapy likely to be effective for treatment of medical condition in the subject as an outcome of the graph neural network, predicted clinical outcome for the subject having the medical condition, and likelihood of at least one certain genetic mutation of the target tissue.

According to a second aspect, a computer implemented method of training a graph neural network that generates an outcome of at least one of: selecting a therapy for treating a medical condition of a person, predicting prognosis of a medical condition, and predicting genetic mutations of a target tissue, comprising: for each of a plurality of sample individuals: receiving a plurality of images of at least one slide depicting at least a portion of the target tissue of the respective sample individual depicting the medical condition stained with a plurality of stains indicative of respective biomarkers, creating a plurality of segmentations, by segmenting for each of the plurality of images, into a plurality of cell type segmentations, and a plurality of region type segmentations, extracting, for each of the cell type segmentations, a plurality of cell phenotype features from an analysis of the plurality of stains, clustering the cell type segmentations according to at least one clustering requirement to create a plurality of clusters, assigning, to at least one of: each respective cell type segmentation and each respective cluster, a feature vector including the cell phenotype features extracted for the respective segmentation, and an indication of a location of the cell type segmentation relative to one or more region type segmentations, creating a cell-graph based on the feature vectors of the plurality of at least one of: cell type segmentations and clusters, wherein each node of the graph denotes at least one of: respective cell type segmentation and respective cluster, each node includes associated corresponding feature vector, and edges of the graph represent a physical distance between the at least one of: cell type segmentations and clusters corresponding to the respective nodes, creating a training dataset including, for each respective sample individual, the cell-graph, and at least one of: an indication of an therapy administered to the respective sample individual, a clinical outcome of the respective sample individual treated with the therapy, a prognosis for the respective sample individual, and an indication of at least one certain genetic mutation of the target tissue of the respective sample individual, and training a graph neural network using the training dataset.

According to a third aspect, a computer implemented method of selecting a therapy for at least one of: treating a medical condition of a person, predicting prognosis of a medical condition, and predicting genetic mutations of a target tissue, comprises: receiving a plurality of images of at least one slide depicting at least a portion of the target tissue of the person depicting the medical condition stained with a plurality of stains indicative of respective biomarkers, creating a plurality of segmentations, by segmenting for each of the plurality of images, into a plurality of cell type segmentations, and a plurality of region type segmentations, extracting, for each of the cell type segmentations, a plurality of cell phenotype features from an analysis of the plurality of stains, assigning, to at least one of: each respective cell type segmentation, a feature vector including the cell phenotype features extracted for the respective segmentation, and an indication of a location of the cell type segmentation relative to one or more region type segmentations, creating a cell-graph based on the feature vectors of the plurality of cell type segmentations, wherein each node of the graph denotes a respective cell type segmentation, each node includes associated corresponding feature vector, and edges of the graph represent a physical distance between cell type segmentations corresponding to the respective nodes, inputting the cell-graph into a graph neural network trained on a training dataset including, for each of a plurality of sample individuals, a plurality of graphs, an indication of an therapy administered to the respective sample individual and at least one of: a clinical outcome of the respective subject individual treated with the therapy, a prognosis for the respective subject, an indication of at least one certain genetic mutation of the target tissue of the respective subject, and obtaining at least one of: an indication of a target therapy likely to be effective for treatment of medical condition in the subject as an outcome of the graph neural network, predicted clinical outcome for the subject having the medical condition, and likelihood of at least one certain genetic mutation of the target tissue.

In a further implementation form of the first, second, and third aspects, the graph further includes a plurality of nodes each denoting a respective region type segmentation, and the edges of the graph further represent a physical distance between one or more of: between cell type segmentations and region type segmentations corresponding to the respective nodes, and between region type segmentations corresponding to the respective nodes.

In a further implementation form of the first, second, and third aspects, the at least one clustering requirement includes a requirement that each respective cluster includes only a single respective cell type segmentation.

In a further implementation form of the first, second, and third aspects, further comprising: identifying most influencing features and/or regions of the graph that most influence the outcome of the graph neural network, determining histological features corresponding to the identified most influencing features and/or regions of the graph, wherein a mapping maps between the histological features and the outcome, and generating a set of instructions to be followed by a user for manually determining the outcome by manually identifying the histological features from an input image, and using the mapping.

In a further implementation form of the first, second, and third aspects, the therapy is selected from the group consisting of: immunotherapy, chemotherapy, radiation therapy, the medical condition is selected from the group consisting of: cancer, and the target comprises cancerous tissue.

In a further implementation form of the first, second, and third aspects, the medical condition is selected from a group consisting of: Non-Alcoholic SteatoHepatitis (NASH), Inflammatory bowel disease (IBD), an autoimmune condition, an inflammatory condition, an immune based condition, and the target is predicting disease prognosis.

In a further implementation form of the first, second, and third aspects, further comprising administering the target immunotherapy for treating the subject for cancer.

In a further implementation form of the first, second, and third aspects, the cells types are selected from the group consisting of: immune cells, sub-types of immune cells, T cells, B cells, lymphocytes, macrophages, platelets, cancer cells, red blood cells, blood vessels, bone cells, fat cells, muscle cells, connective tissue cells, fibroblasts, epithelial cells, non-immune-non-cancer cells.

In a further implementation form of the first, second, and third aspects, the region types are selected from the group consisting of: blood vessels, bone, fat, muscle, connective tissue, lymph node, stroma, tumor region, tumor microenvironment.

In a further implementation form of the first, second, and third aspects, the cell phenotype features are at least one of: stains within the respective segmentation, and a size and/or stain intensity of the respective segmentation stained with a respective stain, nuclear stain intensity of each cell within the respective segmentation, membrane stain intensity of each cell within the respective segmentation, and an indication of cell morphology of each cell within the respective segmentation.

In a further implementation form of the first, second, and third aspects, the cell phenotype features are selected from the group consisting of: size and/or stain intensity of cancer cells expressing a certain biomarker that indicates suppressed immune cell activity, size and/or stain intensity of cancer cells expressing checkpoint inhibitor antigen biomarker that suppresses immune cell activity.

In a further implementation form of the first, second, and third aspects, the at least one clustering requirement includes one or more members selected from a group consisting of: according to cell type, according to at least one of the cell phenotype features, relative location within the image, and according to location of the cell type segmentation relative to the region type segmentation.

In a further implementation form of the first, second, and third aspects, further comprising: extracting, for each of the plurality of clusters, a plurality of cluster phenotype features, wherein the feature vector for at least one of: the respective cell type segmentation and the respective cluster, includes the cell cluster phenotype features of the cluster of the respective cell type segmentation.

In a further implementation form of the first, second, and third aspects, the cluster phenotype features are computed from an aggregation of the cell type segmentations of the respective cluster.

In a further implementation form of the first, second, and third aspects, the cluster phenotype features are selected from a group consisting of: a number of cell type segmentations of the respective cluster, an average size and/or distribution of cell type segmentations of the respective cluster, an average location and/or location distribution and/or density of cell type segmentations of the respective cluster within the image, an average intensity and/or intensity distribution of at least one stain of the cell type segmentations of the respective cluster.

In a further implementation form of the first, second, and third aspects, further comprising extracting, for combinations of cell clusters, a plurality of cluster-to-cluster features, wherein the feature vector for the at least one of: the respective segmentation and the respective cluster, includes the cluster-to-cluster features of the cluster of the respective cell type segmentation.

In a further implementation form of the first, second, and third aspects, the cluster-to-cluster features are computed for at least two clusters, using the respective cluster phenotype features of the at least two clusters.

In a further implementation form of the first, second, and third aspects, the cluster-to-cluster features are selected from the group consisting of: physical distance between clusters, statistical distance between clusters, similarity between clusters, and differences between clusters.

In a further implementation form of the first, second, and third aspects, the graph is created by linking K nearest neighbor nodes, or nodes up to a predefined distance.

In a further implementation form of the first, second, and third aspects, further comprising: obtaining, for the person, personal data include at least one member selected from the group consisting of: omics data, medical history, and demographic data, and inputting a combination of the cell-graph and the personal data into the graph neural network, wherein the training dataset used to train the graph neural network includes personal data for each of the plurality of sample individuals.

In a further implementation form of the first, second, and third aspects, further comprising inputting a combination of a type of cancer of the subject and the cell-graph into the graph neural network, wherein the training dataset used to train the graph neural network includes a plurality of cancer types for each of the plurality of sample individuals.

In a further implementation form of the first, second, and third aspects, further comprising: wherein the segmenting is performed for a plurality of images depicting a plurality of slides obtained from a volume of tissue by a parallel slicing process, computing, for each segmentation, a set of three dimensional (3D) coordinates denoting location within the volume, and wherein each node is associated with the set of 3D coordinates and the physical distance of the edges of the graph is computed as distance within the volume between the 3D coordinates of the respective nodes.

In a further implementation form of the first, second, and third aspects, each of the plurality of images includes slides stained with different stains indicative of respective biomarkers.

In a further implementation form of the first, second, and third aspects, further comprising: registering a plurality of images depicting a plurality of slides obtained from a volume of tissue by a parallel slicing process depicting a plurality of stains indicative of respective biomarkers, to create a single 2D image, wherein the segmenting is performed for the 2D image.

In a further implementation form of the first, second, and third aspects, further comprising: inputting a combination of a selected therapy for treating the subject and the cell-graph into the graph neural network, and obtaining a predicted clinical outcome for the subject when treated with the selected therapy.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DETAILED DESCRIPTION

Figure 1:
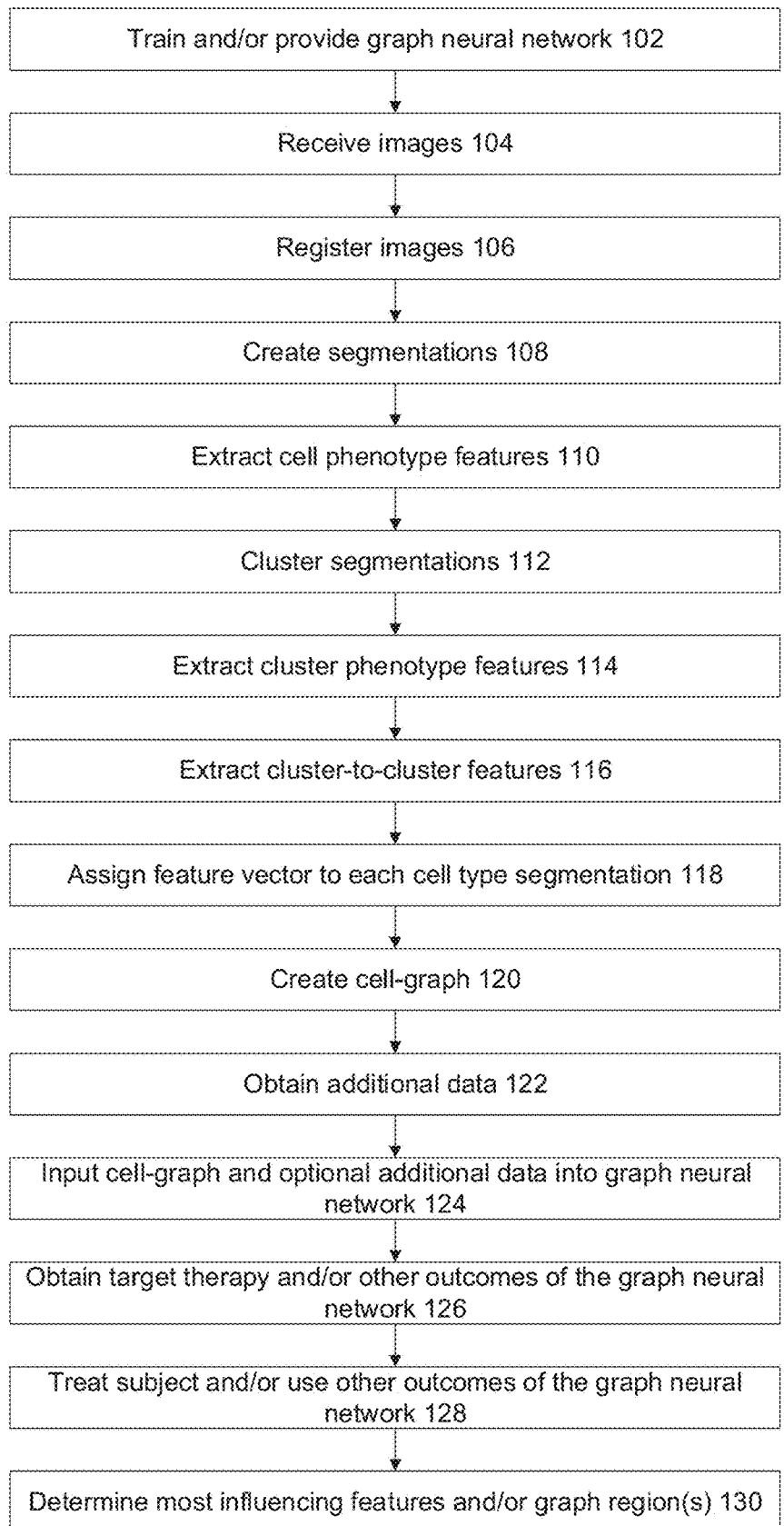
FIG. 1 is a flowchart of a method of selecting a therapy for treating a medical condition using a graph neural network, in accordance with some embodiments of the present invention.

The present invention, in some embodiments thereof, relates to medical therapies and, more specifically, but not exclusively, to systems and methods for selection of an effective therapy for treating a medical condition in a subject and/or for predicting of clinical prognosis and/or for predicting likelihood of a genetic mutation present in a target tissue.

An aspect of some embodiments of the present invention relates to systems, methods, an apparatus, and/or code instructions for selecting a treatment for a medical condition of a patient and/or for predicting of clinical prognosis and/or for predicting likelihood of a genetic mutation present in a target tissue. For example, selecting an immunotherapy for treating cancer, predicting survival in a patient with an autoimmune disease, and/or predicting likelihood of a rare genetic mutation in a target tissue of a patient. The medical condition may be an immune associated condition (i.e., where immune cells are affected), for example, an autoimmune condition (e.g., inflammatory bowel disease (IBD)), cancer (e.g., malignancy of any condition), and/or inflammatory condition (e.g., non-alcoholic fatty liver disease (NASH)).

Images of one or more slides depicting at least a portion of a target tissue (e.g., cancer) of the person depicting the medical condition stained with biomarker stains is received.

Multiple segmentations are created. The images are segmented into cell type segmentations of different cell types, for example, immune cells, sub-types of immune cells, T cells, B cells, lymphocytes, macrophages, platelets, cancer cells, red blood cells, blood vessels, bone cells, fat cells, muscle cells, connective tissue cells, fibroblasts, and epithelial cells. The images may also be segmented into region type segmentations of different regions, for example, blood vessels, bone, fat, muscle, connective tissue, lymph node, stroma, tumor region, and tumor microenvironment. For each of the cell type segmentations, cell phenotype features are extracted based on an analysis of the biomarker stains, for example, which biomarkers are depicted within the respective segmentation, intensity of the respective biomarker stain, and the like. The cell type segmentations are optionally clustered according to at least one clustering requirement to create multiple clusters, for example, segmentations of the same cell type are clustered into a common cluster. Optionally, cluster phenotype features are extracted for each cluster. The cluster phenotype features may be computed from an aggregation of the cell type segmentations of the respective cluster, for example, number of cell type segmentations in the cluster, and/or size of the cluster based on the size and/or distribution of the cell type segmentations therein. Optionally, cluster-to-cluster features are extracted for different combinations of cell clusters. The cluster-to-cluster features may be computed for two or more clusters, using the respective cluster phenotype features of the two or more clusters, for example, physical distance between the clusters, and/or similarity between the clusters. A feature vector including the cell phenotype features, and/or cluster phenotype features, and/or cluster-to-cluster features extracted for the respective cell type segmentation and/or the respective cluster and/or the respective region type, is computed. The feature vector may include an indication of a location of the respective cell type segmentation and/or cluster relative to one or more region type segmentations, for example, an immune cell located within a cancer region, and/or cluster of immune cells within the cancer region. The feature vector is assigned to each cell type segmentation and/or to each cluster. A cell-graph (sometimes referred to herein as graph) is created based on the feature vectors. Each node of the graph denotes a respective cell type segmentation and/or a cluster (e.g., as described herein) and the corresponding assigned feature vector. Edges of the graph represent a physical distance between the cell type segmentations and/or clusters corresponding to the respective nodes. The cell-graph is inputted into a graph neural network trained on a training dataset including, for each of multiple sample individuals, a respective graph (computed as described herein), and one of more of: an indication of a therapy administered to the respective sample individual, a medical condition of the respective sample individual (which may be different than the medical condition of the subject and/or there may be sample individuals with no medical conditions), a clinical outcome of the respective subject individual treated with the therapy, a prognosis of the medical condition in the subject (e.g., regardless of treatment, such as with no treatment, or with treatment), and an indication of genetic mutation of the target tissue of the respective subject (e.g., certain mutations, such as RET fusion, NTRK fusion). At least one of: an indication of a target therapy likely to be effective for treatment of medical condition in the subject, prognosis, and likelihood of one or more certain genetic mutation, is obtained as an outcome of the graph neural network. The subject may be treated for the medical condition using the target therapy and/or according to the likelihood of the certain genetic mutation. Alternatively, the subject may not be treated with strong medications, for example, when the clinical prognosis is good without treatment and/or with mild medications.

At least some implementations of the systems, methods, apparatus, and/or code instructions described herein relate to the technical and/or medical problem of selecting an effective therapy for treating a medical condition in a person, for example, selecting a therapy for treating an immune-based medical condition (e.g., autoimmune, inflammatory, cancer), selecting an immunotherapy for treating cancer, optionally a particular type of cancer (e.g., skin cancer, breast cancer, colon cancer, skin cancer). The same therapy, when used to treat the same type of medical condition, may be effective in one person, and ineffective in another person. It is unclear why the same therapy is effective on certain populations and ineffective on other patient populations. Therefore, it is unclear how to select the therapy which is likely to be effective in the person for treatment of the medical condition.

At least some implementations of the systems, methods, apparatus, and/or code instructions described herein relate to the technical and/or medical problem of detecting certain mutations in the target tissue. Examples of mutations include: RET fusion, and NTRK fusion. The mutations may be rare, making it more difficult/expensive to test for them. The mutations may indicate likelihood of success of the treatment, for example, the immunotherapy treatment is selected based on which mutation is in the cancer cells. In standard practice, mutations are detected by performing genetic sequencing of the cells, which is time consuming and/or expensive. At least some implementations of the systems, methods, apparatus, and/or code instructions described herein enable predicting likelihood of the presence of one or more certain mutations in the target tissue using images, from which a graph is computed and inputted into the graph neural network. The likelihood of the presence of one or more certain mutations in the target tissue is an outcome of the graph neural network.

At least some implementations of the systems, methods, apparatus, and/or code instructions described herein relate to the technical and/or medical problem of predicting prognosis of a subject having a medical condition. The medical condition may develop in different ways in different people, especially when strong treatment (e.g., chemotherapy), or mild therapy (e.g., steroids, alternatively treatments), or no treatment is used. For example, some patients may live for many years when the disease (e.g., autoimmune) subsides with mild or no treatment, while others may die early even with aggressive treatment.

At least some implementations of the systems, methods, apparatus, and/or code instructions described herein may further relate to the technical and/or medical problem of predicting prognosis of the medical condition and/or therapeutic response to a selected therapy. For example, in oncology, it is challenging to accurately predict cancer progression and/or therapeutic response, which makes it difficult to select the proper immunotherapy for treatment of cancer in a subject. Malignancy is a multifactorial, three-dimensional, phenomena, profoundly affected by the complex interplay between tumor-cell and the tumor microenvironment (TME). Current attempts to model this TME are insufficient, considerably due to the fact that omics technologies disrupt the tissue level spatial context of the TME admixture. The same immunotherapy, when used to treat the same type of cancer, may be effective in one person, and ineffective in another person. It is unclear why the same immunotherapy is effective on certain populations and ineffective on other patient populations. Therefore, it is unclear how to select the immunotherapy which is likely to be effective in the person.

At least some implementations of the systems, methods, apparatus, and/or code instructions described herein improve the field of medicine and/or the technical field of machine learning, by provided a graph neural network that provides as an outcome, a therapy (e.g., immunotherapy) likely to effectively for treating a medical condition (e.g., cancer) of a subject, and/or predicting clinical outcome (e.g., prognosis, therapeutic response) optionally for a selected therapy, for example, where the user wishes to evaluate prognosis and/or response to a candidate therapy.

The technical solution and/or the technical improvement provided by at least some implementations of the systems, methods, apparatus, and/or code instructions described herein is different than existing attempted solutions. Standard procedures are manually performed by pathologists, with or without semi-automated cell counting software. These methods are laborious, unscalable, subjective and lack the infrastructure to integrate multi layered data. For example, automated cell counters are based on optics and image analysis to automatically count cells. The amount of data collected is minimal, for example, only the number of cells, which cells are dead and which are alive, and possibly size of the cells. In some approaches the cells are automatically segmented. Features indicating relationships between cells are not obtained. Other methods are based on analyzing genomic and/or proteomic data. Such methods based on omics data disrupt the tissue level spatial context of the TME admixture. Yet another method simply looks at density of CD3 and CD8 cell types in the invasive tumor margin seen in the tissue biopsy to compute an immunoscore which predicts prognosis in colon cancer.

The technical solution and/or the technical improvement provided by at least some implementations of the systems, methods, apparatus, and/or code instructions described herein is based on the computed cell-graph which is inputted into a trained graph neural network. The cell-graph is created from tissue type segmentations and/or region type segmentations of images of slides of target tissue obtained from the subject (e.g., biopsy of cancer). Cell phenotype features are extracted from the segmentations. The segmentations are clustered. Cluster phenotype features may be extracted from the clusters. Cluster-to-cluster features may be extracted for combinations of two or more clusters. A feature vector is computed for each segmentation. The feature vector includes the extracted features corresponding to the respective segmentation, and an indication of a location of the cell type segmentation relative to one or more region type segmentations. The cell-graph is created based on the feature vectors and the segmentations, where each node of the graph denotes a respective segmentation and corresponding feature vector. Edges of the graph represent a physical distance between the segmentations corresponding to the respective nodes. The extracted features and creation of the cell-graph, which is then inputted into the graph neural network, may capture the tissue level spatial context, for example, of the TME admixture, and enable discovery of hidden cellular patterns within the TME (e.g. including the tumor and surrounding immune cells, fibroblasts, and vasculature) which are predictive of cancer progression and/or therapeutic response and/or indicative of an immunotherapy likely to be effective for treating the cancer.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
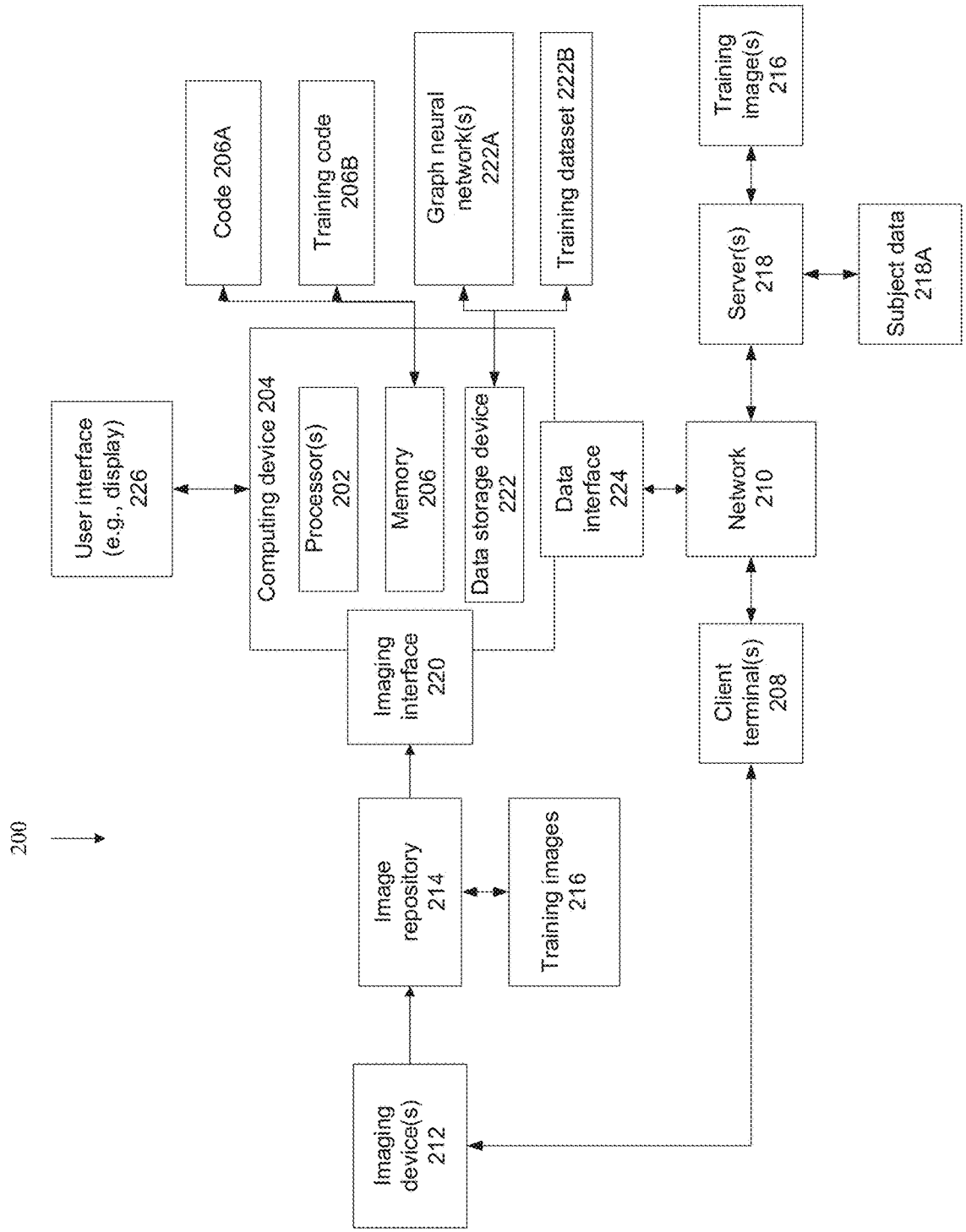
FIG. 2 is a block diagram of components of a system for selecting a therapy for treating a medical condition using a graph neural network and/or for training the graph neural network that generates an outcome of an effective therapy for treating the medical condition, in accordance with some embodiments of the present invention.
Figure 3:
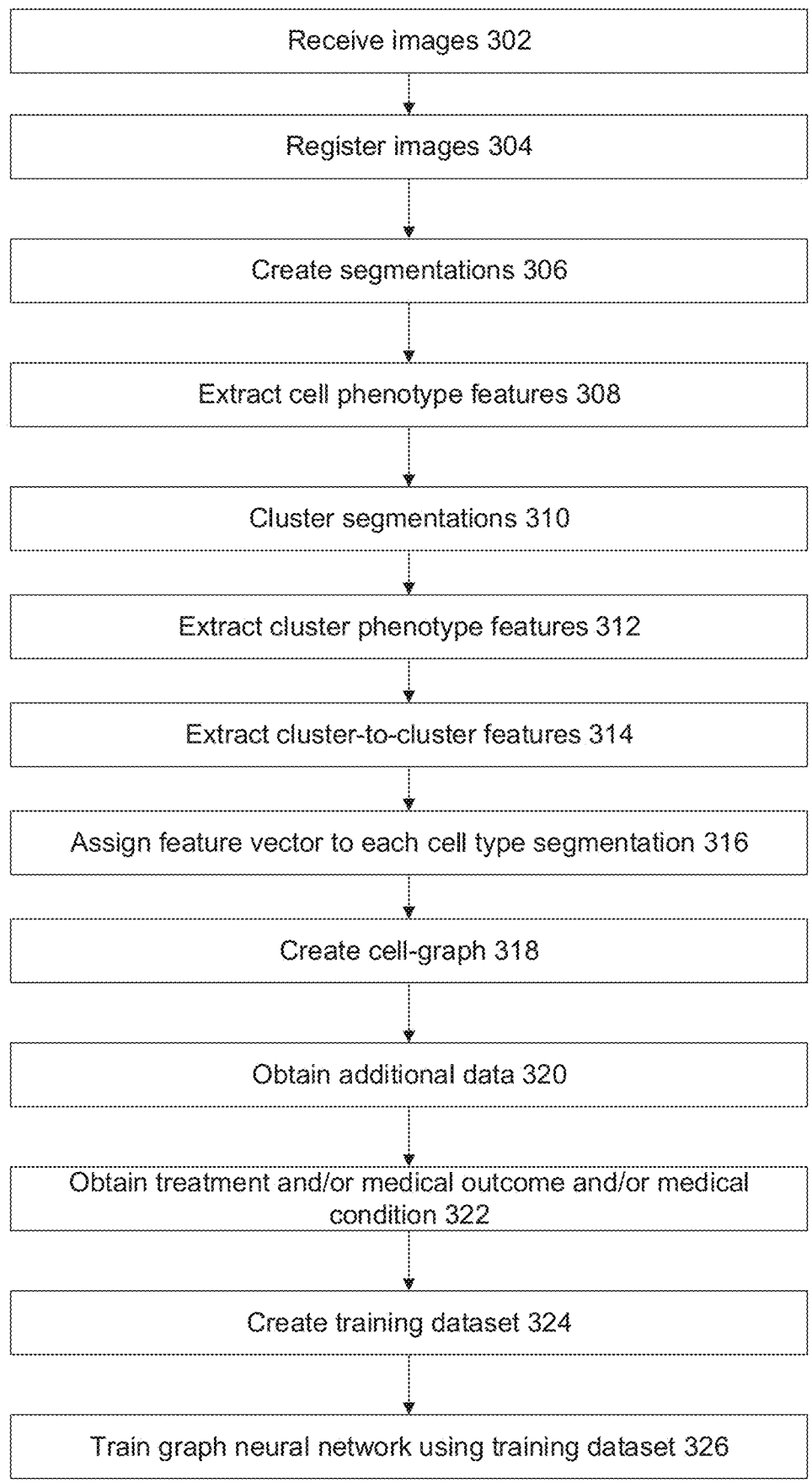
FIG. 3 is a flowchart of an exemplary method for training the graph neural network that generates an outcome of an effective therapy for treating the medical condition, in accordance with some embodiments of the present invention.
Figure 4:
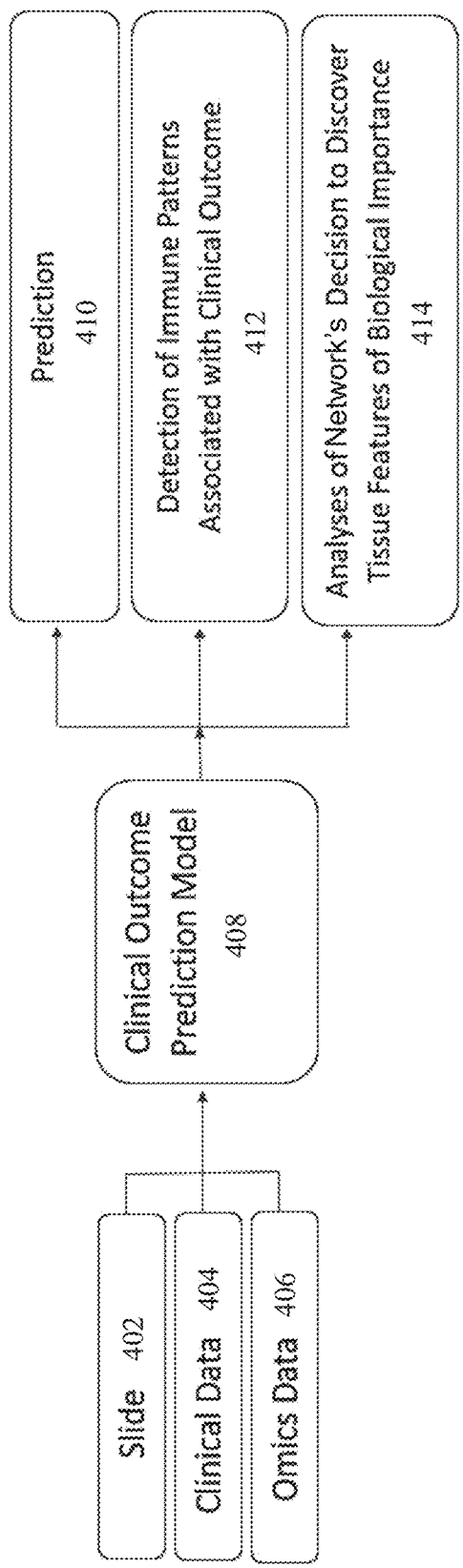
FIG. 4 is a flowchart of another process for multiple uses of the graph neural network, in accordance with some embodiments of the present invention.
Figure 5:
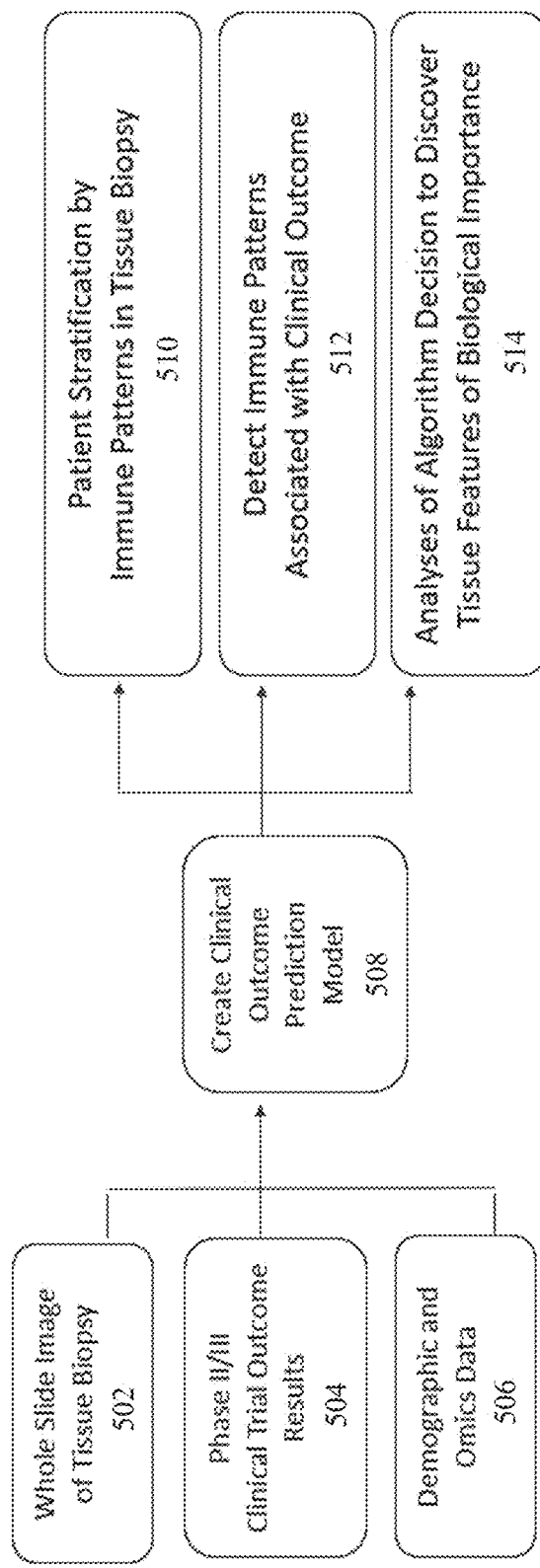
FIG. 5 is a flowchart of yet another process for multiple uses of the graph neural network, in accordance with some embodiments of the present invention.
Figure 6:
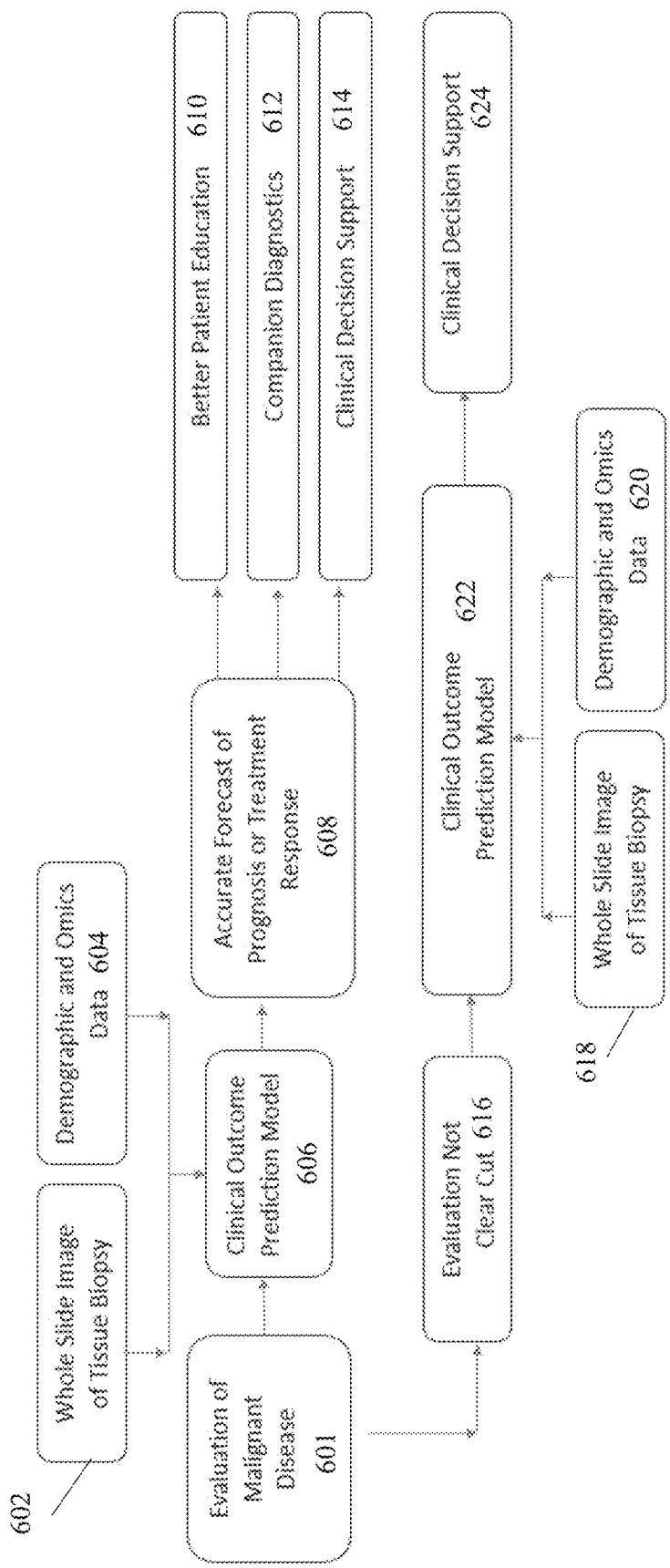
FIG. 6 is a flowchart of yet another process for multiple uses of the graph neural network, in accordance with some embodiments of the present invention.

Reference is now made to FIG. 1, which is a flowchart of a method of selecting a therapy for treating a medical condition using a graph neural network, in accordance with some embodiments of the present invention. Reference is also made to FIG. 2, which is a block diagram of components of a system 200 for selecting a therapy for treating a medical condition using a graph neural network and/or for training the graph neural network that generates an outcome of an effective therapy for treating the medical condition, in accordance with some embodiments of the present invention. Reference is also made to FIG. 3, which is a flowchart of an exemplary method for training the graph neural network that generates an outcome of an effective therapy for treating the medical condition, in accordance with some embodiments of the present invention. Reference is also made to FIG. 4, which is a flowchart of another process for multiple uses of the graph neural network, in accordance with some embodiments of the present invention. Reference is also made to FIG. 5, which is a flowchart of yet another process for multiple uses of the graph neural network, in accordance with some embodiments of the present invention. Reference is also made to FIG. 6, which is a flowchart of yet another process for multiple uses of the graph neural network, in accordance with some embodiments of the present invention.

System 200 may implement the acts of the method described with reference to FIG. 1 and/or FIG. 3, optionally by a hardware processor(s) 202 of a computing device 204 executing code instructions 206A and/or 206B stored in a memory 206.

At least some of the systems and/or methods described herein may implemented and/or integrated features and/or components described with reference to PCT Patent Application Publication No. WO2019/026081 "SYSTEMS AND METHODS FOR ANALYSIS OF TISSUE IMAGES", by at least one common inventor of the present disclosure, incorporated herein by reference in its entirety.

Computing device 204 may be implemented as, for example, a client terminal, a server, a virtual server, a laboratory workstation (e.g., pathology workstation), a procedure (e.g., operating) room computer and/or server, a virtual machine, a computing cloud, a mobile device, a desktop computer, a thin client, a Smartphone, a Tablet computer, a laptop computer, a wearable computer, glasses computer, and a watch computer. Computing 204 may include an advanced visualization workstation that sometimes is implemented as an add-on to a laboratory workstation and/or other devices for presenting indications of the analyzed tissue images and/or other computer added detections to the user (e.g., pathologist, oncologist).

Computing device 204 may include locally stored software that performs one or more of the acts described with reference to FIG. 1 and/or FIGS. 3-6, and/or may act as one or more servers (e.g., network server, web server, a computing cloud, virtual server) that provides services (e.g., one or more of the acts described with reference to FIG. 1 and/or FIGS. 3-6) to one or more client terminals 208 (e.g., remotely located laboratory workstations, remote picture archiving and communication system (PACS) server, remote electronic medical record (EMR) server, remote tissue image storage server, remotely located pathology computing device, client terminal of a user such as a desktop computer) over a network 210, for example, providing software as a service (SaaS) to the client terminal(s) 208, providing an application for local download to the client terminal(s) 208, as an add-on to a web browser and/or a tissue imaging viewer application, and/or providing functions using a remote access session to the client terminals 208, such as through a web browser. In one implementation, multiple client terminals 208 each obtain images of the slides from different imaging device(s) 212. Each of the multiple client terminals 208 provides the images to computing device 204, and receives back a respective indication of an effective therapy and/or predicted clinical outcome for a certain therapy (e.g., candidate therapy selected by the user). In another implementation, code 206A and/or graph neural network 222A are implemented by computing device 204 which receives tissue images from imaging device 212, and provides the indication of the effective therapy and/or predicted clinical outcome for a certain therapy, for example, for presentation on a display (e.g., 226). Is it noted that the training of the graph neural network, and the analysis of tissue images by the trained graph neural network, may be implemented by the same computing device 204, and/or by different computing devices 204, for example, one computing device trains the graph neural network, and transmits the trained neural network to a server device for analysis of tissue images.

Computing device 204 receives tissue images captured by one or more imaging device(s) 212. Exemplary imaging device(s) 212 include: a scanner scanning in standard color channels (e.g., red, green blue), a multispectral imager acquiring images in four or more channels, a confocal microscope, and/or other imaging devices as described herein, a black a white imaging device, an imaging sensor. Multiple images may be acquired for the same slide, for example, depicting different biomarker stains. Additional exemplary imaging device(s) 212 are described with reference to 104 of FIG. 1.

Imaging device(s) 212 creates tissue images from physical tissue samples which may be obtained by a tissue extracting device, for example, a fine needle for performing fine needle aspiration (FNA), a larger bore needle for performing a core biopsy, and a cutting tool (e.g., knife, scissors, scoop) for cutting out a sample of the tissue (e.g., tumor removal).

Imaging device(s) 212 may create two and/or three (2D and/or 3D) dimensional tissue images.

Tissue images captured by imaging machine 212 may be stored in an image repository 214, for example, a storage server, a computing cloud, virtual memory, and a hard disk. Training images 216 may be created based on the captured tissue images, as described herein.

Training dataset 222B may be created from training images 216 and other data, including a computed cell-graph and an indication of therapy administered to the respective person, clinical outcome, and/or other additional personal data of the subject 218A such as medical history, omics data, and/or demographic data, as described herein, for example, with reference to 122 of FIG. 1. Training dataset 222B is used to train graph neural network 222A, as described herein.

It is noted that training images 216 may be stored by a server 218, accessibly by computing device 204 over network 210, for example, a publicly available training dataset, tissue images stored in a PACS server and/or pathology imaging server, and/or a customized training dataset created for training the classifiers, as described herein.

Computing device 204 may receive the training images 216 and/or tissue images for analysis from imaging device 212 and/or image repository 214 using one or more imaging interfaces 220, for example, a wire connection (e.g., physical port), a wireless connection (e.g., antenna), a local bus, a port for connection of a data storage device, a network interface card, other physical interface implementations, and/or virtual interfaces (e.g., software interface, virtual private network (VPN) connection, application programming interface (API), software development kit (SDK)). Alternatively or additionally, Computing device 204 may receive the training images 216 and/or tissue images for analysis from client terminal(s) 208 and/or server(s) 218.

Hardware processor(s) 202 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processor(s) 202 may include one or more processors (homogenous or heterogeneous), which may be arranged for parallel processing, as clusters and/or as one or more multi core processing units.

Memory 206 (also referred to herein as a program store, and/or data storage device) stores code instruction for execution by hardware processor(s) 202, for example, a random access memory (RAM), read-only memory (ROM), and/or a storage device, for example, non-volatile memory, magnetic media, semiconductor memory devices, hard drive, removable storage, and optical media (e.g., DVD, CD-ROM). Memory 206 stores code 206A that implements one or more acts and/or features of the method described with reference to FIG. 1, and/or training code 206B that executes one or more acts of the method described with reference to FIG. 3.

Computing device 204 may include a data storage device 222 for storing data, for example, graph neural networks 222A, training dataset 222B, and/or other code such as for segmenting of cells and/or extraction of features (e.g., neural networks and/or other classifiers), as described herein. Data storage device 222 may be implemented as, for example, a memory, a local hard-drive, a removable storage device, an optical disk, a storage device, and/or as a remote server and/or computing cloud (e.g., accessed over network 210). It is noted that execution code portions of the data stored in data storage device 222may be loaded into memory 206 for execution by processor(s) 202.

Computing device 204 may include data interface 224, optionally a network interface, for connecting to network 210, for example, one or more of, a network interface card, a wireless interface to connect to a wireless network, a physical interface for connecting to a cable for network connectivity, a virtual interface implemented in software, network communication software providing higher layers of network connectivity, and/or other implementations.

Computing device 204 may access one or more remote servers 218 using network 210, for example, to download updated training images 216 and/or to download an updated version of the graph neural network 222A, training code 206B, and/or the training dataset 222B.

Computing device 204 may communicate using network 210 (or another communication channel, such as through a direct link (e.g., cable, wireless) and/or indirect link (e.g., via an intermediary computing device such as a server, and/or via a storage device) with one or more of:

Client terminal(s) 208, for example, when computing device 204 acts as a server providing image analysis services (e.g., SaaS) to remote laboratory terminals, for analyzing remotely obtained tissue images.

Server 218, for example, implemented in association with a PACS and/or electronic medical record, which may storage large numbers of tissue images for analysis and/or which may store personal data of the subject (i.e., subject data) 218A which is inputted into the graph neural network with the graph, as described herein.

Tissue image repository 214 that stores training images 216 and/or tissue images outputted by imaging device 212.

It is noted that imaging interface 220 and data interface 224 may exist as two independent interfaces (e.g., two network ports), as two virtual interfaces on a common physical interface (e.g., virtual networks on a common network port), and/or integrated into a single interface (e.g., network interface).

Computing device 204 includes or is in communication with a user interface 226 that includes a mechanism designed for a user to enter data (e.g., personal data of the subject) and/or view the selected therapy predicted as likely to be effective for the subject. Exemplary user interfaces 226 include, for example, one or more of, a touchscreen, a display, a keyboard, a mouse, and voice activated software using speakers and microphone.

Referring now back to FIG. 1, at 102, a graph neural network(s) is provided and/or trained.

The graph neural network receives as input, the cell-graph computed as described herein.

There may be one or multiple types of graph neural networks. For example, according to medical condition, according to an immune-based medical condition (e.g., autoimmune (e.g., IBD), inflammatory (e.g., NASH), and/or cancer), according to sub-medical conditions, according to treatment types, and/or according to a combination of medical condition (and/or sub-medical condition) and treatment types. For example, the graph neural network may be trained for cancer, optionally a certain type of cancer (e.g., lung cancer, skin cancer, breast cancer, colon cancer), optionally for treatment using immunotherapy (e.g., pembrolizumab) and/or other one or more cancer treatments (e.g., surgical resection, chemotherapy, radiation therapy). In another example, the graph neural network is for immunotherapy for treatment of a certain type of cancer, for example, for Non-Small Cell Lung Cancer (NSCLC) there are several treatment options including pembrolizumab (alone as a single-agent), pembrolizumab and chemotherapy combination, and other immunotherapy options such as: Ipilimumab+nivolumab (Ipi Nivo) or atezolizumab (Atezo). In another example, the graph neural network is for immunotherapy for treatment of any one of multiple types of cancer.

The graph neural network may be trained on a training dataset including, for each of multiple sample individuals, one or more of: a respective cell-graph (computed as described herein), an indication of a therapy administered to the respective sample individual, an indication of the medical condition of the respective sample individual (which may be different than the medical condition of the subject and/or there may be sample individuals with no medical conditions), an indication of prognosis, an indication of one or more genetic mutations in the target tissue, personal data of the subject (e.g., as described with reference to 122 of FIG. 1) a clinical outcome of the respective subject individual with the medical condition treated with the therapy.

The selection of the graph neural network may be performed manually by the user (e.g., via a GUI, for example, via a menu and/or icons of available image analysis code). The selection may be performed automatically by code that analyzes, for example, the tissue image, metadata of the image, and/or other patient data associated with the image such as diagnosis of the medical condition and/or proposed treatment type (e.g., obtained from a PACS server, Digital Imaging and Communications in Medicine (DICOM) data, and/or electronic medical record).

The graph neural network (NN) may be implemented using a suitable architecture, for example, one or more of combination of: fully connected NN, convolutional NN, full convolutional NN, encoder-decoder NN, and/or a combination of multiple sub-architectures, for example, integrated networks, parallel networks, and/or cascade networks. The graph NN may be combined and/or integrated and/or in communication with other machine learning components, for example, support vector machine, clusterization methods, sets of rules, logistic regression, K nearest neighbors, and decision trees.

An exemplary method of training the graph neural network is described with reference to FIG. 3.

at 104, one or more images of one or more slides are received.

The image(s) of slide(s) depict at least a portion of a target tissue of the person stained with multiple stains indicative of presence of biomarkers in the stained cells, and/or depicting biomarkers in the stained cells (sometimes referred to herein as biomarker stains, or stains). The target tissue depicts the medical condition, for example, cancerous tissue, such as a tumor and/or other malignancy. Additional non-target tissues are depicted in the images, for example, immune cells, types of different immune cells, and non-target-non-immune cells such as other cells of the body for example red blood cells, blood vessel cells, muscle cells, bone cells, fibroblasts, epithelial cells, and connective tissue cells.

The tissue may be obtained intra-operatively, during for example, a biopsy procedure, a FNA procedure, a core biopsy procedure, colonoscopy for removal of colon polyps, surgery for removal of an unknown mass, surgery for removal of a benign cancer, and/or surgery for removal of a malignant cancer, surgery for treatment of the medical condition. Tissue may be obtained from fluid, for example, urine, synovial fluid, blood, and cerebral spinal fluid.

Tissue may be in the form of a connected group of cells, for example, a histological slide. Tissue may be in the form of individual or clumps of cells suspended within a fluid, for example, a cytological sample.

The images may be obtained, for example, from an image sensor that captures the images, from a scanner that captures images, from a server that stores the images (e.g., PACS server, EMR server, pathology server). For example, tissue images are automatically sent to analysis after capture by the imager and/or once the images are stored after being scanned by the imager.

The images may be whole slide images (WSI). The images may be of slides created from a tissue biopsy obtained from the individual.

Each slide may be stained with one or more biomarker stains, for example, immunohistochemistry (IHC), fluorescence, Hematoxylin and Eosin (H&E), Multiplex Ion Beam Imaging (MIBI), and the like.

One or more images may be captured for each slide, for example, using different imaging modalities, which may capture different images of the same slide based on different stains. The images for each slide may be multiplexed, for example, stored as multiple channels.

Optionally, the tissue image created from the physical slide with tissue thereon is a color image, optionally including multiple channels for each pixel, for example, 3 (e.g., RGB) or more channels (e.g., multispectral, confocal, fluorescent). Optionally, the tissue image is created based on visible light energy. For example, capturing a digital image of a view as seen under a light microscope. Alternatively or additionally, the tissue image is created based on other radiation wavelengths, for example, near infrared, short wave infrared, and the like.

The tissue may be arranged on a slide. A frozen section may be created and sliced for creating multiple slides. Tissue may be stained.

The slides may include histology slides and/or cytology slides.

The tissue may be chemically stained for increased visibility for generation of the tissue image. Alternatively or additionally, the tissue itself is not stained, but rather imaging methods are used that do not necessarily require staining, for example, a spectral imager.

As used herein, the term biomarker stain sometimes refers to actual staining of the tissue, and/or to 'virtual staining' of tissues where the tissue itself is not actually stained but different imaging methods are used that do not necessarily require staining. It is noted that different imaging methods may be combined with different biomarker stains to create multiple combinations of biomarker stains and imaging modalities.

Optionally, a set of colors associated with the chemical staining and/or virtual staining (e.g., by a multispectral imager) is identified. The set of colors may be stored, for example, in a dataset according to the chemical staining and/or virtual staining. The set of colors may be automatically identified by code and/or manually designated by the user according to the chemical and/or virtual staining. The identified set of colors may be used for segmenting tissue versus non-tissue background, and/or for cell type segmentation, as described herein in additional detail. The identified set of colors may be stored, for example, in a LAB color space, RGB color space, and/or other color spaces. It is noted that LAB color space is more linear than RGB color space.

The tissue image may be created by imaging the tissue with the imaging device. Optionally, slides including the prepared tissue are imaged by the imaging device.

Optionally, the tissue slides are imaged at high magnification, for example, between about X200-X400, or about X100-400, or about X100-X200, or about X100, or about X200, or about X400, or other values. Such high magnification imaging may create very large images, for example, on the order of Giga Pixel sizes. Such large tissue images of the entire slide may be referred to herein as Whole Slide Images (WSI).

The imaging device may be implemented as, for example, a spectral imager, such as a multispectral (few to tens of channels) or a hyperspectral (up to hundreds of channels). The multispectral imager creates tissue images with 4 or more spectrum frequencies, which is noted to be higher than the 3 spectrums of a normal imager (e.g., imaging in red, green, and blue (RGB). The imager may produce a spectral signature including multiple channels for each pixel, in contrast for example, to the 3 channels (e.g., RGB) obtained by the traditional staining process. The image analysis code described herein may be created and/or trained according to the spectral signature of each pixel. It is noted that alternatively, a standard imager imaging in 3 channels (e.g., RGB) may be used, and/or a black and white imager may be used.

Alternatively or additionally, the imaging device is implemented based on a Stimulated Raman scattering (SRS) microscopy. The spectral image (cube) acquired by a spectral imager, or a SRS microscope, may be analyzed by combining morphological based method with spectral based methods to improve the outcome of traditional image analysis methods relying purely on RGB images.

Alternatively or additionally, a mapping and/or other transformation function is estimated between the colors (e.g., RGB) of an image of stained tissue and the spectrum corresponding to the same location. The mapping may be used to produce a virtual stained slide from a spectral image of a fresh tissue slide.

Multiple tissue images of the tissue may be provided, for example, from the same biopsy, of different stains, of the same body fluid, a slices from a sequential slicing (e.g., frozen section). The multiple tissue images may be arranged as a single 3D tissue image, and/or as a set of 2D slices. The multi-slide level tissue type(s) may be computed according to an analysis of the multiple tissue images, as described herein.

The slides may be obtained from a volume (i.e., three dimensions (3D)) of tissue by a parallel slicing process, for example, a knife that slices the volume into parallel slices. The slides (which may be processed as two dimensional (2D) images) are created from the parallel slices. The slides may be obtained from different regions of the volume of tissue, which may lie along the same plane. The different slides may correspond to different regions of the tumor, for example, within the tumor, the external boundary of the tumor, and different surfaces of the tumor.

At 106, the received images of slices may be registered. Registration may be performed in 2D (e.g., mapping corresponding locations and/or structures in the images to the same 2D location) and/or 3D.

Optionally, images depicting multiple slides obtained from the 3D volume of tissue by the parallel slicing process depicting multiple biomarker stains are registered. The registration may be to create a single 2D image, and/or a registered 3D volume. The segmenting (as described herein) is performed for the 2D image and/or for the 3D volume.

At 108, multiple segmentations are computed, by segmenting each of the images.

Optionally, the images are segmented into multiple cell type segmentations. Optionally, each segmentation includes a single cell of a certain cell type. There may be multiple cell types, for example, immune cells, sub-types of immune cells (e.g., T cells, B cells, lymphocytes, macrophages), platelets, cancer cells, red blood cells, blood vessels, bone cells, fat cells, muscle cells, fibroblasts, epithelial cells, connective tissue cells non-immune-non-cancer cells. Cell type segmentations may include bacteria, protozoa, and/or other non-human cells. Cell type segmentations may include cancer cells and/or cells of the target tissue associated with the medical condition.

Alternatively or additionally, the images are segmented into multiple region type segmentations. The region type segmentation may include multiple cells, which may be of different types, and/or may include tissues (or portion thereof) and/or microenvironments. For example, blood vessels, bone tissue, fat tissue, fibroblasts, epithelial cells, muscle tissue, connective tissue, lymph node, stroma, tumor region, tumor microenvironment, microenvironment of the target tissue associated with the medical condition, and the target tissue associated with the medical condition.

Each cell type and/or region time segmentation (e.g., when registered) may corresponding to multiple biomarker stained, for example, each segmentation is registered to multiple images depicting multiple biomarker stains. For example, the same segmented lymphocyte may be depicted in one image with one biomarker stain, and in another image with another biomarker stain.

Optionally, segmentation is performed for the 3D registered volume, i.e., for the images depicting slides obtained from the 3D volume of tissue (e.g., by the parallel slicing process. In such a case, a set of three dimensional (3D) coordinates denoting location of the respective segmentation within the 3D volume may be computed. In such implementation, nodes of the cell-graph (computed as described herein) are associated with the set of 3D coordinates. The physical distance associated with the edges of the graph (as described herein) is computed as the distance within the 3D volume between the 3D coordinates of the respective nodes.

The segmentation may be performed to identify, for example, individual cells, groups of same type of cells, groups of different types of cells, and/or tissues.

The segmentations may be performed by segmentation code, for example, a neural network (e.g., CNN) trained to perform the segmentation using a training dataset of labelled segmentations.

Optionally, each image depicting a respective stain and/or captured by a respective imaging modality may be segmented. When the images are registered, segmentations of the multiple registered images may correspond to the same physical region being segmented, for example, providing a multi-channel segmentation.

Additional exemplary processes for segmenting the images of the slides are described, for example, with reference to WO2019/026081, for example, feature 110 of FIG. 1 of WO2019/026081.

At 110, for each of the segmentations (e.g., cell type and/or region type), one or more cell phenotype features are extracted. The cell phenotype features are extracted based on an analysis of the biomarker stains. Each cell phenotype feature may be extracted from one respective biomarker stain of the corresponding cell type segmentation, and/or a combination of two or more biomarker stains for the corresponding cell type segmentation.

Exemplary cell phenotype features include one or combination of:
  An indication of the type of stain(s) (e.g., biomarker stain) and/or capturing method used within the respective segmentation (e.g., PD-L1 IHC, fluorescence, H&E, MIBI)
  A size depicted within the segmentation (e.g., area, percentage of area within the segmentation) that includes the biomarker stain, stain intensity (e.g., distribution, histogram of number of pixels and corresponding stain intensity) of one or combination of biomarker stains depicted in the respective segmentation stained.
  Stain intensity of one or a combination of biomarkers within each cell within the respective segmentation. The stain intensity may include various intensities such as nuclear or membrane staining intensity. For example—the PD-L1 membrane staining intensity.
  An indication of cell morphology of each cell and/or the nucleus of the cell within the respective segmentation, for example, eccentricity of the respective cell.
  Area of the respective cell and/or the nucleus of the respective cell (e.g., surface area, and/or volume).
  Type and/or classification category of cell, for example, red blood, white blood cell, muscle cell, cancer cell, fibroblasts, epithelial cell, and the like.
  Number of nucleuses and/or number of cell organelles and/or distribution of cell organelles within the cell.

In an example, a cell phenotype features includes size and/or stain intensity of cancer cells expressing a certain biomarker that indicates suppressed immune cell activity. In another example another cell phenotype features includes size and/or stain intensity of cancer cells expressing checkpoint inhibitor antigen biomarker that suppresses immune cell activity.

The extracted cell phenotype features (e.g., as described with reference to 110), and/or extracted cluster phenotype features (e.g., as described with reference to 114), and/or extracted cluster-to-cluster features (e.g., as described with reference to 116) may be handcrafted features, and/or features that are automatically extracted by extracting code. The features may be extracted by a machine learning (ML) model, for example, one or more or combination of neural networks, support vector machines (SVM), decision trees, boosting, random forest, and the like.

At 112, the cell type segmentations are optionally clustered according to one or more clustering requirements, to create multiple clusters. Alternatively, some cell type segmentations are clustered, and some cell type segmentations are not clustered (e.g., may be considered as a cluster only of the respective cell type segmentation). Alternatively, no clusters are created. In an implementation where no clusters are created, the clustering requirement may define that each cluster includes only the respective cell type segmentation. I.e., each cell type segmentation may be considered its own individual cluster (for further processing as described herein), which effectively defines that no clustering is performed, i.e., there are no clusters with two or more members.

Optionally, all cell type segmentations of a same cluster meet a common clustering requirement. Exemplary clustering requirement includes one or more of:
  According to respective cell types of the cell type segmentations, i.e., all cell type segmentations of the same cluster are of the same cell type, for example, all T cells are clustered together, all cancer cells are clustered together.
  According to a combination of cell types, e.g., all T cells and B cells are clustered together, or all macrophages and blood vessel cells are clustered together, or immune cells (of a general immune cell type, or a specific immune cell type such as T cell, B cell, macrophage) and cancer cells are clustered together, and/or all immune cells are clustered together.
  According to the cell phenotype features. I.e., all cell type segmentations having the same cell phenotype feature are included in a common cluster, for example, all cell type segmentations having a visible nucleus larger than a certain size (e.g., threshold) in the H&E stain are in a common cluster.
  According to a combination of cell phenotype features, for example, all cell type segmentations having both a nucleus larger than a certain size and have PD-L1 positive staining are in a common cluster.
  Relative location within the image. For example, all cell type segmentations located within a circle of a certain diameter are in a common cluster.
  Location of the cell type segmentation relative to the region type segmentation, for example, all immune cells located within the tumor region are in one cluster, all immune cells located on the border of the tumor region are in another cluster, and all cancer cells within blood vessels are in yet another cluster.

Optionally, each segmentation (i.e., cell type and/or region type) is associated with a location coordinates, for example, x,y (and/or z) Cartesian and/or polar coordinates within the image and/or slide. The coordinates may be used to compute the relative locations, locations, and/or distances described herein.

Alternatively or additionally, the region type segmentations are clustered according to one or more clustering requirements, to create multiple clusters, for example, by type of region and/or combination of regions. For example, all region type segmentations depicting a tumor/cancer region are clustered into a common cluster. In another example, region type segmentations depicting blood vessels within a tumor region are clustered into a common cluster. Alternatively, the region type segmentations are not clustered.

Alternatively or additionally, the cell type and region type segmentations are clustered according to one or more clustering requirements, to create multiple clusters. Each cluster may include both cell type and region type segmentations.

Optionally, at 114, one or more cluster phenotype features may be extracted for each of the clusters. The cluster phenotype features may be computed from an aggregation of the segmentations (e.g., cell type and/or region type) which are members of the respective cluster.

Exemplary cluster phenotype features include one or more or combination of:

- A number of segmentations (e.g., cell type and/or region type) members of the respective cluster, i.e., number of cell type segmentation members in the T cell cluster.
- An average size and/or distribution of segmentation members (e.g., cell type and/or region type) of the respective cluster, optionally based on cell phenotype features of members within the respective cluster, for example, for a cluster of immune cells, the number of cells of each type of immune cell (e.g., number of T cells, number of macrophages, and the like).
- An average location and/or location distribution and/or density of segmentations (e.g., cell type and/or region type) that are members of the respective cluster within the image.
- An average intensity and/or intensity distribution and/or density of at least one biomarker of the segmentations (e.g., cell type and/or region type) members of the respective cluster, for example, average intensity and/or distribution of intensity of a certain biomarker within members of the respective cluster. In another example, number of segmentation members that depict each type of biomarker.
- According to cell phenotype features, which are different than the cell phenotype features that were used to create the clusters (since all members of the cluster have the same such cell phenotype feature used to create the cluster).

Optionally, at 116, one or more cluster-to-cluster features are extracted for different combinations of two or more cell clusters. For example, cluster-to-cluster features may be computed for a pair of clusters, and/or cluster-to-cluster features may be computed for a set of three or more clusters. Multiple combinations of two or more clusters may be considered.

Exemplary cluster-to-cluster features include:

- Physical distance between clusters, for example, between the closest points of the clusters, between the furthest points of the clusters, between the center (e.g., center of mass) of the clusters.
- Statistical distance between clusters. For example, computed using a statistical comparison function, such as a function that compares statistical distance between distributions.
- Similarity between clusters. For example, computed using a similarity comparison function, such as a function that compares statistical similarity between distributions.
- Differences between clusters. For example, computed using a difference comparison function, such as a function that compares statistical difference between distributions.

Cluster-to-cluster features may be computed using the respective cluster phenotype features of the two clusters, for example, statistical distance and/or similarity and/or difference between the two clusters using one or more respective cluster phenotype features of each of the clusters. In an example, statistical distance and/or similarity and/or difference between a first distribution of a certain biomarker intensity within a first cluster and a second distribution of the same certain biomarker within a second cluster. In another example, statistical distance and/or similarity and/or difference between a distribution of location of T cells within a cancer region, and distribution of location of T cells external to the cancer region.

At 118, a feature vector is computed. The feature vector may be associated with each respective segmentation (i.e., cell type and/or region type) and/or with each respective cluster. Optionally, the feature vector is only for the cell type segmentations. Alternatively, the feature vector is only for the region type segmentations. Alternatively or additionally, the feature vector is for the computed clusters. Alternatively, there are two or more types of feature vectors, for example, one feature vector type for the cell type segmentations, and/or another feature vector type for the region type segmentations and/or another feature vector type for the clusters. Alternatively, the feature vector is a combination of two or more of the cell type segmentation, the region type segmentations, and the clusters.

The feature vector includes one or more of: the cell phenotype features extracted for the respective segmentation, an indication of a location of the respective segmentation (e.g., cell type) relative to one or more other segmentation types (e.g., region type, another cell type segmentations of another cell type), a physical distance between the respective segmentation and the one or more other segmentation types, the cell cluster phenotype features of the cluster of the respective segmentation, and/or the cluster-to-cluster features of the cluster of the respective cell type segmentation.

At 120, a cell-graph is computed (i.e., created) based on the feature vectors of the segmentations.

Optionally, the cell-graph includes only the cell type segmentations. Alternatively, the cell-graph includes only the region type segmentations. Alternatively, the cell-graph includes only the computed clusters. Alternatively, two or more cell-graphs are created, one cell-graph type for the cell type segmentations, and/or another cell-graph type for the region type segmentations, and/or another graph for the clusters. Alternatively, the cell-graph includes a combination of the cell type segmentation, the region type segmentations, and the clusters.

Each node of the cell-graph denotes one or more of a respective cell type segmentation, a respective region type segmentation, and a respective cluster. Each node corresponds to the assigned (e.g., associated) feature vector. Edges of the cell-graph, that connect nodes of the cell-graph, may represent a physical distance between the respective segmentation (i.e., cell type and/or region type and/or cluster) corresponding to the respective node. In region type the physical distance may be computed, for example, as a shortest distance between the regions and/or distance between region centers. In clusters the physical distance may be computed, for example, by physical distance between cluster centers. The physical distance may be: between cell type segmentations and region type segmentations corresponding to the respective nodes, between region type segmentations and region type segmentations corresponding to the respective nodes, between cell type segmentations and cell type segmentations corresponding to the respective nodes, between computed clusters representing respective nodes. The physical distance may be measured, for example, in micrometers based on the actual distance on the slide, in pixels of the image, and/or other units.

The graph may be created, for example, by linking K nearest neighbor nodes, and/or nodes up to a predefined distance.

Optionally, at 122, additional personal data of the subject may be obtained, for example, automatically from a dataset (e.g., EMR, PACS server), and/or manually entered (e.g., via a user interface).

Exemplary additional personal data of the subject includes one or more of:

Clinical data of the subject, for example, medical history, demographic data, omics data, age, gender, tumor stage, and the like.

Exemplary omics data includes: genetic mutations, microsatellite instability, and the like.

A proposed therapy for treatment of the subject. The proposed therapy may be a general modality type of therapy and/or combination thereof, for example, one or combination of: immunotherapy, chemotherapy, and radiation therapy. The prosed therapy may be a particular type of therapy and/or combination thereof, for example, a certain combination of chemotherapy drugs, a certain immunotherapy drug, and/or combination of the certain chemotherapy drugs and certain immunotherapy drug.

Type of medical condition, for example, general medical condition, such as cancer. The type of medical condition may be a specific type, such as a sub-type of the general medical condition, for example, type of cancer, such as colon cancer, breast cancer, lung cancer, and skin cancer.

At 124, the cell-graph(s) is inputted into the graph neural network. Multiple graphs may be inputted, for example, in parallel into corresponding inputs of the graph neural network, as a combination into a single input of the graph neural network.

Optionally, a combination of the cell-graph and the personal data (one or more personal data of the subject as described with reference to 122 of FIG. 1) are inputted into the graph neural network, for example, in parallel into corresponding inputs of the graph neural network, as a combination into a single input of the graph neural network.

Optionally, the cell-graph and the personal data are inputted into a first layer of the graph neural network. Alternatively, the cell-graph is inputted into a first layer of the graph neural network, and the personal data is inputted into one or more internal layers (e.g., hidden layers) of the neural network, and/or into the last layer of the neural network. The layers prior to the layer where the personal data is inputted may perform an embedding and/or dimensionality reduction of the cell-graph.

At 126, an outcome of the cell-graph is obtained. The outcome may include one or more of the following:

An indication of a target therapy likely to be effective for treatment of medical condition in the subject. When the medical condition is cancer, the therapy may be a certain immunotherapy drug and/or type (e.g., class) of immunotherapy drug. The target therapy may be an outcome of the graph neural network when no candidate therapy is inputted into the graph neural network, i.e., the graph neural network selects the best therapy. The outcome of the graph neural network may include a predicted clinical outcome for the subject when treated with the target therapy selected by the graph neural network.

A predicted prognosis as an outcome of the cell-graph when treated with the candidate treatment (when the candidate treatment is inputted into the graph neural network, or the graph is built to provide outcome for the specific candidate treatment). For example, the user wishes to evaluate the clinical outcome for the candidate treatment.

A value indicative of likelihood of effectiveness of the target therapy in the subject, for example, a probability value in the range of 0-100%.

Detecting immune patterns associated with clinical outcome, additional tissue features of biological importance, companion diagnostics, and/or other outcomes, as described herein, for example, with reference to FIGS. 4-6.

Prognosis for the subject, for example, how long the subject is predicted to survive, whether the subject will recover or no, quality of life of the subject, and the like.

Predicted genetic mutations that may be present, for example, in the target issue, for example, in the cancer cells. The predicted genetic mutations may be rare, for example, NTRK, RET fusion, and the like.

The outcome of the cell-graph may be, for example, presented on a display (e.g., within a user interface such as a graphical user interface), stored in a data storage device (e.g., within the EMR of the subject and/or the PACS server in association with the images), forwarded to another computing device and/or server, and/or provided to another process as input (e.g., a health management application).

At 128, the subject is treated and/or other outcomes of the graph neural networks are used. Optionally, the target therapy (an outcome of the graph neural network) and/or the candidate therapy (which was evaluated as the outcome of the graph neural network) may be administered to the subject for treatment of the medical condition. For example, the target immunotherapy and/or candidate immunotherapy is administered to the subject for treatment of cancer. The predicted mutation may be obtained and used in decision making, for example, used to select the immunotherapy treatment to be administered. The prognosis may be obtained and used in decision making, for example, to help the subject decide whether to be treated or not, or with which treatment.

At 130, the most influential features and/or region graphs that most influence the outcome (as would otherwise be generated by the graph neural network) may be identified and translated into corresponding histological features may be manually determined by a user (e.g., pathologist) viewing the images of the slides.

One or more components of the feature vectors of the graph (e.g., certain features of the feature vectors) and/or regions of the graph that most affect (e.g., have highest correlation with) the outcome of the graph neural network are identified. A mapping between the most influencing features and/or region of the graph and histological features of the image slides may be generated. The histological features represent features that a human is capable of performing manually by viewing the images and/or simple arithmetic, for example, number of cells of a certain type in a certain region of the image, for example, number of T cells located within the tumor divided by number of T cells located outside the tumor. Alternatively or additionally, a mapping between the histological features and outcome (that would otherwise be provided by the graph neural network) is generated. The outcome may be predicted using the histological features. The mapping(s) may be implemented, for example, using one or more of: a simple set of rules, a function, a table, a set of pointers, and/or a trained classifier trained on a suitable training dataset.

A set of instructions to be followed by a user for manually determining the histological features from an input image, and/or another set of instructions for manually predicting the outcome from the histological features, may be generated. The instructions may include the mapping dataset(s), for example, a simple computation for predicting the outcome from the histological features. Instructions may be generated, for example, using natural language processing (NLP) approaches. The instructions may be presented on a user interface, for example, text instructions presented on a display and/or printed, a video graphically depicting the instructions (e.g., rendered animation), and/or audio instructions played over a microphone. The user (e.g., pathologist) may manually predict the outcome by manually following the instructions for extracting the relevant histological features from an input image. For example, the instructions are to obtain the histologic features of (i) a counted number of certain immune cells external to the tumor region, and (ii) a counted number of other immune cells within the tumor region. The instructions for predicting the outcome may be, for example, to divide the value of histological feature (i) by the value of histological feature (ii), and compare to a threshold. When the value resulting from the division is above a threshold, a certain immunotherapy is likely to work for this subject, and/or when the value resulting from the division is below the threshold, a different immunotherapy is likely to work for this subject.

Alternatively or additionally, other outcomes of the graph neural network are used. Exemplary outcomes are described herein, for example, with reference to FIGS. 4-6.

Referring now back to FIG. 3, features described with reference to 302-322 are performed for each subject of multiple subjects:

At 302, one or more images of one or more slides are received, for example, as described with reference to 104 of FIG. 1.

At 304, the received images of slices may be registered, for example, as described with reference to 106 of FIG. 1.

At 306, multiple segmentations are computed, for example, as described with reference to 108 of FIG. 1.

At 308, one or more cell phenotype features are extracted for each of the segmentations (e.g., cell type and/or region type), for example, as described with reference to 110 of FIG. 1.

At 310, the cell type segmentations and/or region type segmentations are clustered according to one or more clustering requirements, for example, as described with reference to 112 of FIG. 1.

Optionally, at 312, one or more cluster phenotype features may be extracted for each of the clusters, for example, as described with reference to 114 of FIG. 1.

Optionally, at 314, one or more cluster-to-cluster features are extracted for different combinations of two or more cell clusters, for example, as described with reference to 116 of FIG. 1.

At 316, a feature vector associated with each respective segmentation (i.e., cell type and/or region type) is computed, for example, as described with reference to 118 of FIG. 1.

At 318, a cell-graph is computed based on the feature vectors of the segmentations, for example, as described with reference to 120 of FIG. 1.

At 320, additional personal data of the subject may be obtained, for example, as described with reference to 122 of FIG. 1.

At 322, an indication of the medical condition of the subject, and/or the treatment administered to the subject, and/or the medical outcome of the subject in response to the treatment administered to the subject is provided, and/or prognosis, and/or presence of defined mutations in the target tissue, for example, manually entered by a user (e.g., via a user interface) and/or automatically extracted from data stored in a data storage device (e.g., from the EMR of the subject, diagnostic codes, billing codes, and the like).

At 324, one or more training datasets are created, for example, as described with reference to 102 of FIG. 1.

At 326 one or more graph neural networks are trained using the training dataset(s), for example, as described with reference to 102 of FIG. 1.

Referring now back to FIG. 4, at 402, images of slides are obtained, for example, as described with reference to 104 of FIG. 1.

At 404, clinical data of the subject is obtained, for example, as described with reference to 122 of FIG. 1.

At 406, omics data of the subject is obtained, for example, as described with reference to 122 of FIG. 1.

At 408, the images, are processed as described with reference to FIG. 1, to compute the graph, which is fed in combination with the clinical data and/or omics data into the graph neural network. As used herein, the phrase "*Clinical Outcome Prediction Model*" refers to the process described with reference to one or more of 104-124 FIG. 1, of computing the graph, and/or the trained graph neural network into which the graph and/or other data are inputted.

At 410, a prediction of clinical outcome for the subject is obtained as an outcome of the Clinical Outcome Prediction Model, which refers to the graph neural network and/or related processing for example, as described with reference to 104-124 of FIG. 1. The predicted clinical outcome may include, for example, an indication of whether the subject is responding to treatment with a certain immunotherapy (e.g., when the immunotherapy is provided an input into the Clinical Outcome Prediction Model, for example, a binary value indicative of yes or no, and/or a percentage likelihood model on a range of 0-100%, or other categories (e.g., somewhat responding, average response, good response). In another example, the predicted clinical outcome includes an estimated number of years of progression free survival.

Alternatively or additionally, at 412, detected immune patters associated with the clinical outcome are obtained as an outcome of the Clinical Outcome Prediction Model. For example, local density of a certain immune cell associated with prognosis and/or treatment response.

Alternatively or additionally, at 414, the Clinical Outcome Prediction Model (e.g., graph neural network's outcome and/or internal data (e.g., embedding extracted from hidden layers) and/or clusters and/or feature) is analyzed to discover tissue features of biological importance. For example, explainability and/or interpretability methods are used to detect tissue features that determined the decision of the clinical outcome prediction model.

Referring now back to FIG. 5, at 502, images of slides, optionally whole slide images of tissue biopsies, are obtained, for example, as described with reference to 104 of FIG. 1.

At 504, phase II and/or III clinical trial outcome results are obtained. For example, an indication of the subject's clinical outcome (e.g., yes—responded to treatment, or no—did not response to treatment), and/or estimated years of progression free survival.

At 506, demographic and/or omics data of the subject is obtained, for example, as described with reference to 122 of FIG. 1.

At 508, graphs are created using the slide images, the phase II/III clinical trial outcome results, and optionally the demographic and/or omics data of the subject, and included in a training dataset, and a graph neural network is trained using the training dataset, for example, as described with reference to FIG. 3.

At 510, patient stratification by immune patterns in tissue biopsy is performed based on an outcome of the Clinical Outcome Prediction Model (e.g., using the output of the graph neural network, embeddings extracted from hidden layers of the graph neural network, and/or using the features and/or clusters described herein). For example, tumors that have or don't have immune cell clusters, tumors lymphocyte rich vs. lymphocyte depleted, spatial structures present or absent, and the like.

Alternatively or additionally, at 512, detected immune patters associated with the clinical outcome are obtained as an outcome of the Clinical Outcome Prediction Model. For example, local density of a certain immune cell associated with prognosis. For example, as described with reference to 130 of FIG. 1.

Alternatively or additionally, at 514, the Clinical Outcome Prediction Model (e.g., graph neural network's outcome and/or internal data (e.g., embedding extracted from hidden layers) and/or clusters and/or feature) is analyzed to discover tissue features of biological importance. For example, explainability and/or interpretability methods are used to detect tissue features that determined the decision of the clinical outcome prediction model. For example, as described with reference to 130 of FIG. 1.

Referring now back to FIG. 6, the Clinical Outcome Prediction Model created for a certain organ and/or cancer type (e.g., as described with reference to FIGS. 1 and/or 3) may be used in other environments and/or for other applications. For example, in the clinical setting, at 601, the oncologist performs the standard clinical evaluation of malignant disease (e.g., imaging, staging, grading, and the like) the oncologist may use the Clinical Outcome Prediction Model as part of the initial cancer patient evaluation, and/or utilize the Clinical Outcome Prediction Model in certain cases in which there are no clear guidelines.

An exemplary process for using the Clinical Outcome Prediction Model as part of the initial cancer patient evaluation is now described.

At 602, images of slides, optionally whole slide images of tissue biopsies, are obtained, for example, as described with reference to 104 of FIG. 1.

At 604, demographic and/or omics data of the subject is obtained, for example, as described with reference to 122 of FIG. 1.

At 606, the images, are processed as described with reference to FIG. 1, to compute the graph, which is fed in combination with the demographic and/or omics data into the graph neural network, for example, as described with reference to 106-124 of FIG. 1.

At 608, an accurate forecast of prognosis and/or treatment response for the subject is obtained as an outcome of the graph neural network. For example, an indication of whether the subject is responding to treatment with a certain immunotherapy (e.g., when the immunotherapy is provided an input into the Clinical Outcome Prediction Model, for example, a binary value indicative of yes or no, and/or a percentage likelihood model on a range of 0-100%, or other categories (e.g., somewhat responding, average response, good response). In another example, the predicted clinical outcome includes an estimated number of years of progression free survival.

At 610, the forecast of prognosis and/or treatment response is used for better patient education, for example, treatment options and/or survival forecast.

Alternatively or additionally, at 612, a companion diagnostic may be performed based on the forecast of prognosis and/or treatment response, for example, to detect the treatment most suitable for the subject.

Alternatively or additionally, at 614, clinical decision making is support based on the forecast of prognosis and/or treatment response.

An exemplary process for using the Clinical Outcome Prediction Model in certain cases in which there are no clear guidelines 616 is now described. For example, in certain cases in which the standard evaluation reveals that the patient's tumor (e.g., type, stage, etc.) does not have clear clinical management guidelines (e.g., chemotherapy in stage 3 colon cancer), the oncologist may use the Clinical Outcome Prediction Model for clinical decision support.

At 618, images of slides, optionally whole slide images of tissue biopsies, are obtained, for example, as described with reference to 104 of FIG. 1.

At 620, demographic and/or omics data of the subject is obtained, for example, as described with reference to 122 of FIG. 1.

At 622, the images, are processed as described with reference to FIG. 1, to compute the graph, which is fed in combination with the demographic and/or omics data into the graph neural network, for example, as described with reference to 106-124 of FIG. 1.

At 624, a more accurate forecast of the subject's clinical outcome (e.g., yes/no treatment response, estimated years of progression free survival, etc.) obtained as an outcome of the Clinical Outcome Prediction Model may be used by the oncologist for detecting the treatments that are most suitable for the patient and/or supporting the process of clinical decision making (e.g., a bad prognosis according to the model may suggest the administration of chemotherapy in stage 3 colon cancer).

Various embodiments and aspects of implementations of the systems, methods, apparatus, and/or code instructions as delineated hereinabove and as claimed in the claims section below find experimental support in the following examples.

EXAMPLES

Reference is now made to the following examples, which together with the above descriptions illustrate some implementations of the systems, methods, apparatus, and/or code instructions described herein in a not necessarily limiting fashion.

Inventors performed an experiment based on at least some implementations of the systems, methods, apparatus, and/or code instructions described herein to evaluate the hypothesis that an analysis of Tumor-infiltrating lymphocytes (TILs) in the Tumor Microenvironment (TME) predicts prognosis of early stage ER+breast cancer patients.

Methods

Inventors examined 399 ER+ stage I-II breast cancer patients with whole slide images (WSI) available from TCGA database. 276 patients (70%) were used for training and 123 patients (30%) for validating the model.

Digital structuring of WSIs, including automated detection of lymphocytes, tumor and tumor adjacent stroma, was performed using a novel deep learning-based semantic segmentation system (Nucleai, Tel Aviv).

A Cox Survival analysis was used to detect prognostic spatial features, corresponding to the cell phenotype features and/or cluster phenotype features and/or cluster-to-cluster features described herein. Prognosis was defined as progression free interval (PFI)—the time between diagnosis to progression or death.

A principal component analysis (PCA) was used to reduce and decorrelate significant features. The resulting PCA features were used to fit the final model.

The model was then validated on an independent database of 42 WSI of breast lumpectomies from two tertiary hospitals in Israel—Sheba Medical Center and Kaplan Medical Center.

Results

The detection performance for tumor area and lymphocytes in the TCGA validation set reached scores of 99% and 97% respectively, in comparison to human annotation.

In a Kaplan-Meier (KM) analysis, several spatial features, like a high number of TIL clusters were significantly associated with longer PFI (P<0.005). In a multivariate analysis, the model remained significantly associated with PFI after adjusting to age and stage, in both the training and validation sets.

Inventors used the model to determine a high and a low risk groups. The rates of distant recurrence at 10 years in the low-risk, and high-risk groups were 3% vs 16% (P<0.001).

The independent validation cohort was underpowered. However, in a preliminary analysis low risk patients had longer PFI (P=0.046).

Figure 7:
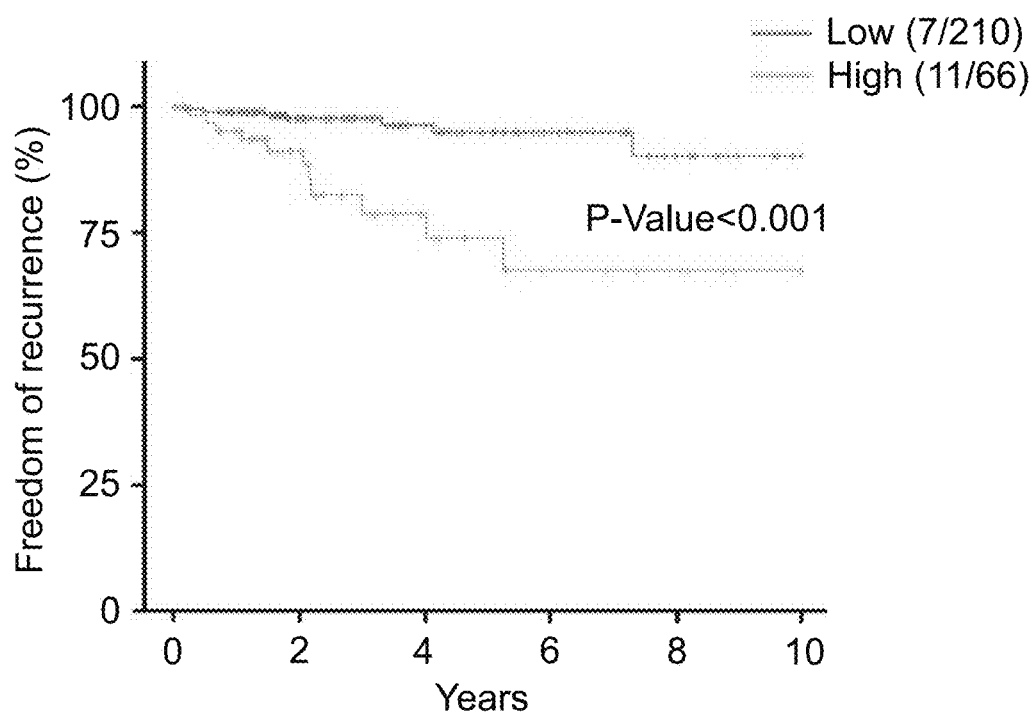
FIG. 7 is a table and chart presenting experimental results, in accordance with some embodiments of the present invention.

Reference is now made to FIG. 7, which is a table 702 and chart 704 presenting results of a multivariate Cox Proportional Analysis of Age, Stage and prognostic score in relation to progression free interval, for the experiment, in accordance with some embodiments of the present invention.

Figure 8:
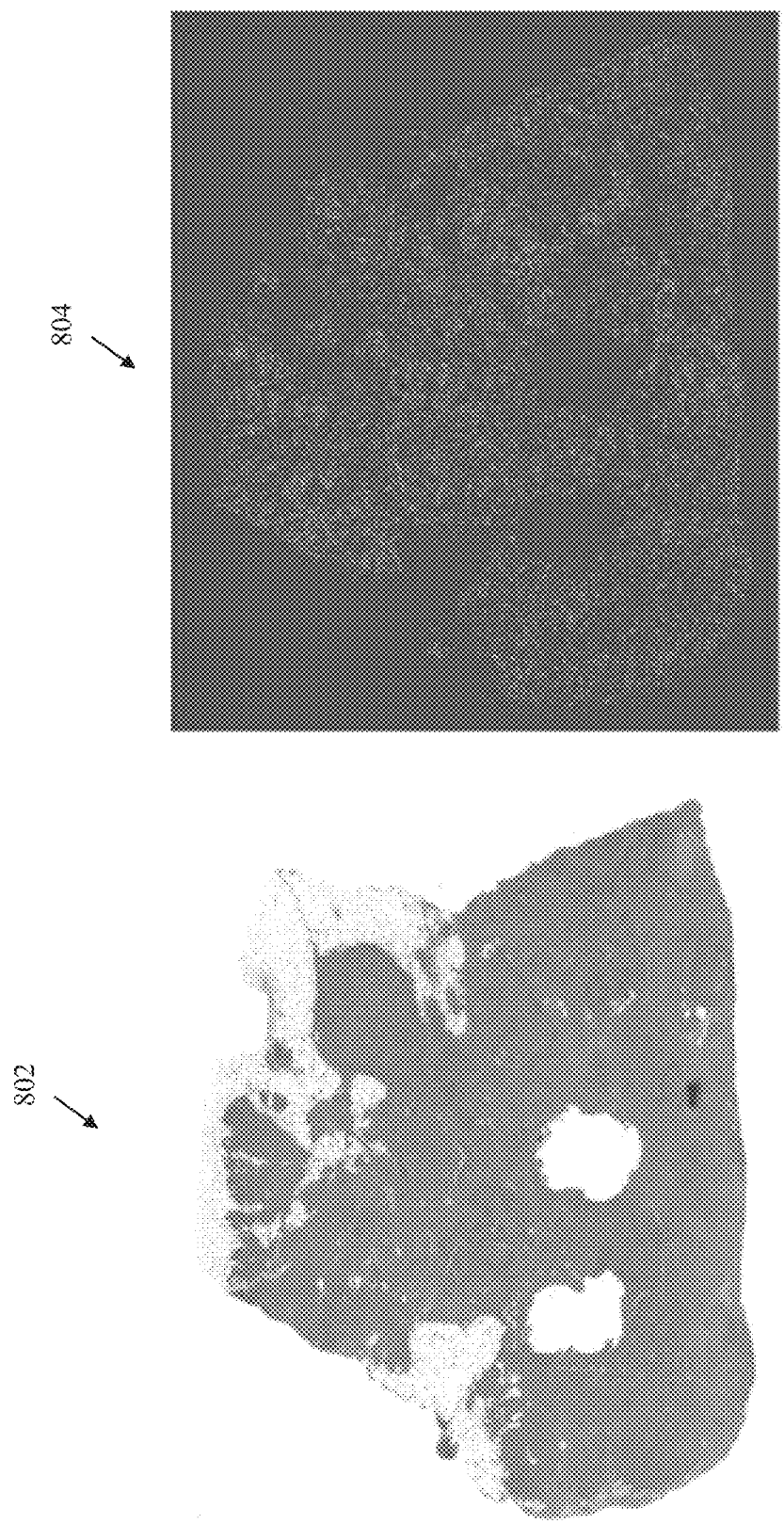
FIG. 8 is an image of a biopsy of a subject identified as a low risk patient and a heatmap showing a high density of Tumor-infiltrating lymphocytes (TILs) for the experiment, in accordance with some embodiments of the present invention.

Reference is now made to FIG. 8, which is an image of a biopsy 802 of a subject identified as a low risk patient by at least some implementations of the systems, methods, apparatus, and/or code instructions described herein, and a heatmap 804 showing a high density of TILs (PFI: 2632 days), for the experiment, in accordance with some embodiments of the present invention.

Figure 9:
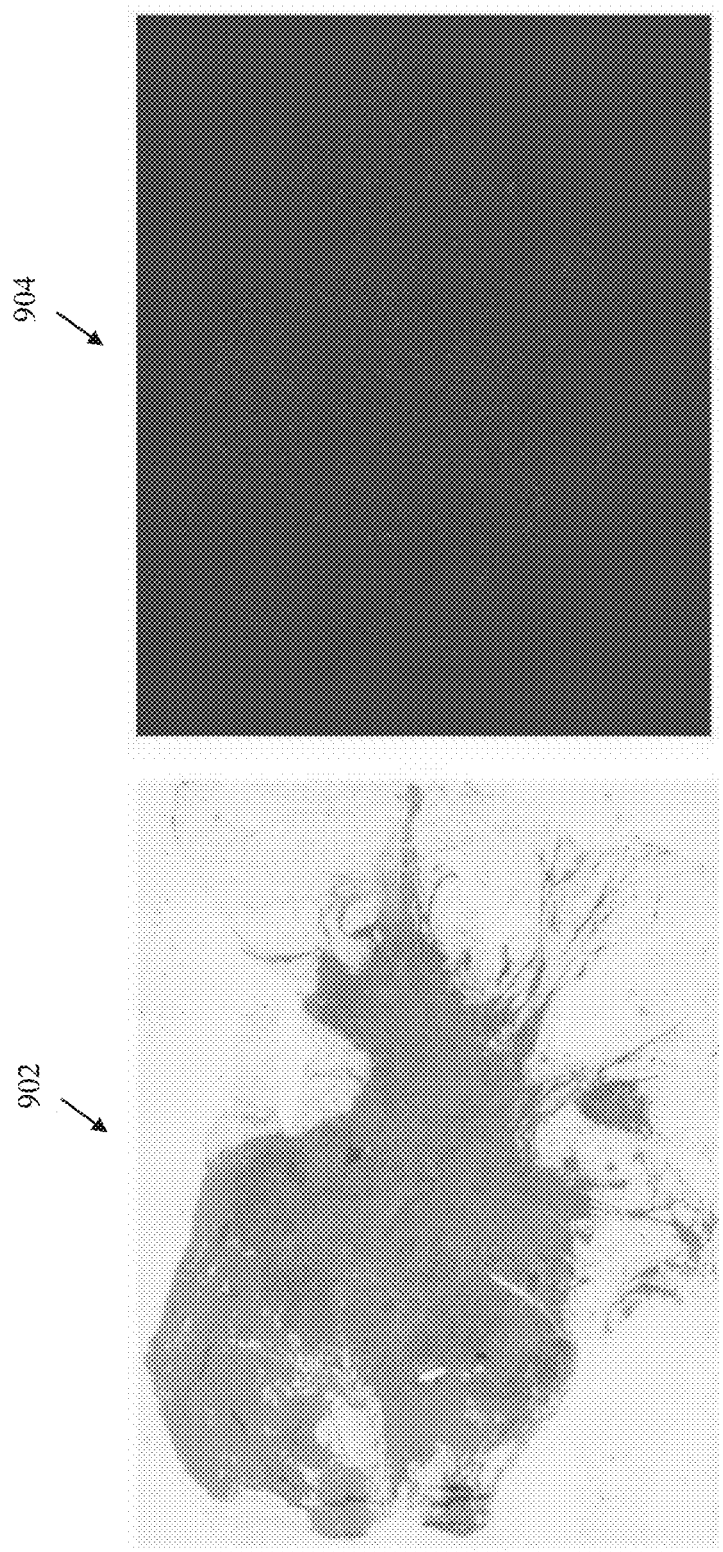
FIG. 9 is an image of a biopsy of a subject identified as a high risk patient and a heatmap showing a low density of TILs for the experiment, in accordance with some embodiments of the present invention.

Reference is now made to FIG. 9, which is an image of a biopsy 902 of a subject identified as a high risk patient by at least some implementations of the systems, methods, apparatus, and/or code instructions described herein, and a heatmap 904 showing a low density of TILs (PFI: 756 days), for the experiment, in accordance with some embodiments of the present invention.

CONCLUSION

Using at least some implementations of the systems, methods, apparatus, and/or code instructions described herein for the characterization of tumor infiltrating lymphocytes in breast cancer biopsies, provides evidence that various spatial features predict patient prognosis.

Higher number of TIL clusters is associated with longer PFI and a lower recurrence rates, suggesting that the spatial organization of the immune system is prognostic for ER+ early stage breast cancer patients.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant graph neural networks will be developed and the scope of the term graph neural network is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

In addition, any priority document(s) of this application is/are hereby incorporated herein by reference in its/their entirety.

What is claimed is:

1. A computer implemented method of at least one of: selecting a therapy for treating a medical condition of a person, predicting prognosis of a medical condition, and predicting genetic mutations of a target tissue, comprising:
    receiving a plurality of images of at least one slide depicting at least a portion of the target tissue of the person depicting the medical condition stained with a plurality of stains indicative of respective biomarkers;
    creating a plurality of segmentations, by segmenting for each of the plurality of images, into a plurality of cell type segmentations, and a plurality of region type segmentations that include tissue level segmentations;
    extracting, for each of the cell type segmentations, a plurality of cell phenotype features from an analysis of the plurality of stains;
    clustering the cell type segmentations according to at least one clustering requirement to create a plurality of clusters;
    assigning, to at least one of: each respective cell type segmentation and each respective cluster, a feature vector including the cell phenotype features extracted for the respective segmentation, and an indication of a location of the cell type segmentation relative to one or more region type segmentations that include tissue level segmentations;
    creating a cell-graph based on the feature vectors of the plurality of at least one of: cell type segmentations and clusters, wherein each node of the graph denotes at least one of: respective cell type segmentation and respective cluster, each node includes associated corresponding feature vector, and edges of the graph represent a physical distance between the at least one of: cell type segmentations and clusters corresponding to the respective nodes;
    inputting the cell-graph into a graph neural network trained on a training dataset including, for each of a plurality of sample individuals, a plurality of graphs, an indication of a therapy administered to the respective sample individual and at least one of: a clinical outcome of the respective subject individual treated with the therapy, a prognosis for the respective subject, an indication of at least one certain genetic mutation of the target tissue of the respective subject; and
    obtaining at least one of: an indication of a target therapy likely to be effective for treatment of medical condition in the subject as an outcome of the graph neural network, predicted clinical outcome for the subject having the medical condition, and likelihood of at least one certain genetic mutation of the target tissue.

2. The method of claim 1, wherein the graph further includes a plurality of nodes denoting espective region type segmentations that includes respective tissue level segmentations, and the edges of the graph further represent a physical distance between one or more of: between cell type segmentations and region type segmentations corresponding to the respective nodes, and between region type segmentations corresponding to the respective nodes.

3. The method of claim 1, further comprising:
    identifying most influencing features and/or regions of the graph that most influence the outcome of the graph neural network;
    determining histological features corresponding to the identified most influencing features and/or regions of the graph, wherein a mapping maps between the histological features and the outcome; and
    generating a set of instructions to be followed by a user for manually determining the outcome by manually identifying the histological features from an input image, and using the mapping.

4. The method of claim 1, at least one of: (i) wherein the therapy is selected from the group consisting of: immunotherapy, chemotherapy, radiation therapy, the medical condition is selected from the group consisting of: cancer, and the target comprises cancerous tissue, and (ii) wherein the medical condition is selected from a group consisting of: Non-Alcoholic SteatoHepatitis (NASH), Inflammatory bowel disease (IBD), an autoimmune condition, an inflammatory condition, an immune based condition, and the target is predicting disease prognosis.

5. The method of claim 1, at least one of: (i) wherein the cells types are selected from the group consisting of: immune cells, sub-types of immune cells, T cells, B cells, lymphocytes, macrophages, platelets, cancer cells, red blood cells, blood vessels, bone cells, fat cells, muscle cells, connective tissue cells, fibroblasts, epithelial cells, non-immune-non-cancer cells, and (ii) wherein the region types are selected from the group consisting of: blood vessels, bone, fat, muscle, connective tissue, lymph node, stroma, tumor region, tumor microenvironment.

6. The method of claim 1, at least one of: (i) wherein the cell phenotype features are at least one of: stains within the respective segmentation, and a size and/or stain intensity of the respective segmentation stained with a respective stain, nuclear stain intensity of each cell within the respective segmentation, membrane stain intensity of each cell within the respective segmentation, and an indication of cell morphology of each cell within the respective segmentation, and (ii) wherein the cell phenotype features are selected from the group consisting of: size and/or stain intensity of cancer cells expressing a certain biomarker that indicates suppressed immune cell activity, size and/or stain intensity of cancer cells expressing checkpoint inhibitor antigen biomarker that suppresses immune cell activity.

7. The method of claim 1, wherein the at least one clustering requirement includes one or more members selected from a group consisting of: according to cell type, according to at least one of the cell phenotype features, relative location within the image, and according to location of the cell type segmentation relative to the region type segmentation, and a requirement that each respective cluster includes only a single respective cell type segmentation.

8. The method of claim 1, further comprising:
extracting, for each of the plurality of clusters, a plurality of cluster phenotype features,
wherein the feature vector for at least one of: the respective cell type segmentation and the respective cluster, includes the cell cluster phenotype features of the cluster of the respective cell type segmentation.

9. The method of claim 8, wherein the cluster phenotype features are computed from an aggregation of the cell type segmentations of the respective cluster.

10. The method of claim 8, wherein the cluster phenotype features are selected from a group consisting of: a number of cell type segmentations of the respective cluster, an average size and/or distribution of cell type segmentations of the respective cluster, an average location and/or location distribution and/or density of cell type segmentations of the respective cluster within the image, an average intensity and/or intensity distribution of at least one stain of the cell type segmentations of the respective cluster.

11. The method of claim 1, further comprising:
extracting, for combinations of cell clusters, a plurality of cluster-to-cluster features,
wherein the feature vector for the at least one of: the respective segmentation and the respective cluster, includes the cluster-to-cluster features of the cluster of the respective cell type segmentation.

12. The method of claim 11, wherein the cluster-to-cluster features are computed for at least two clusters, using the respective cluster phenotype features of the at least two clusters.

13. The method of claim 11, wherein the cluster-to-cluster features are selected from the group consisting of: physical distance between clusters, statistical distance between clusters, similarity between clusters, and differences between clusters.

14. The method of claim 1, wherein the graph is created by linking K nearest neighbor nodes, or nodes up to a predefined distance.

15. The method of claim 1, further comprising:
obtaining, for the person, personal data include at least one member selected from the group consisting of: omics data, medical history, and demographic data, and
inputting a combination of the cell-graph and the personal data into the graph neural network, wherein the training dataset used to train the graph neural network includes personal data for each of the plurality of sample individuals.

16. The method of claim 1, further comprising inputting a combination of a type of cancer of the subject and the cell-graph into the graph neural network, wherein the training dataset used to train the graph neural network includes a plurality of cancer types for each of the plurality of sample individuals.

17. The method of claim 1, further comprising:
wherein the segmenting is performed for a plurality of images depicting a plurality of slides obtained from a volume of tissue by a parallel slicing process,
computing, for each segmentation, a set of three dimensional (3D) coordinates denoting location within the volume, and
wherein each node is associated with the set of 3D coordinates and the physical distance of the edges of the graph is computed as distance within the volume between the 3D coordinates of the respective nodes,
wherein each of the plurality of images includes slides stained with different stains indicative of respective biomarkers.

18. The method of claim 1, further comprising:
inputting a combination of a selected therapy for treating the subject and the cell-graph into the graph neural network; and
obtaining a predicted clinical outcome for the subject when treated with the selected therapy.

19. A computer implemented method of training a graph neural network that generates an outcome of at least one of: selecting a therapy for treating a medical condition of a person, predicting prognosis of a medical condition, and predicting genetic mutations of a target tissue, comprising:
for each of a plurality of sample individuals:
receiving a plurality of images of at least one slide depicting at least a portion of the target tissue of the respective sample individual depicting the medical condition stained with a plurality of stains indicative of respective biomarkers;
creating a plurality of segmentations, by segmenting for each of the plurality of images, into a plurality of cell type segmentations, and a plurality of region type segmentations that include tissue level segmentations;
extracting, for each of the cell type segmentations, a plurality of cell phenotype features from an analysis of the plurality of stains;
clustering the cell type segmentations according to at least one clustering requirement to create a plurality of clusters;
assigning, to at least one of: each respective cell type segmentation and each respective cluster, a feature vector including the cell phenotype features extracted for the respective segmentation, and an indication of a location of the cell type segmentation relative to one or more region type segmentations that include tissue level segmentations;
creating a cell-graph based on the feature vectors of the plurality of at least one of: cell type segmentations and clusters, wherein each node of the graph denotes at least one of: respective cell type segmentation and respective cluster, each node includes associated corresponding feature vector, and edges of the graph represent a physical distance between the at least one of: cell type segmentations and clusters corresponding to the respective nodes;
creating a training dataset including, for each respective sample individual, the cell-graph, and at least one of: an indication of a therapy administered to the respective sample individual, a clinical outcome of the respective sample individual treated with the therapy, a prognosis for the respective sample individual, and an indication of at least one certain genetic mutation of the target tissue of the respective sample individual; and training a graph neural network using the training dataset.

20. A computer implemented method of selecting a therapy for at least one of: treating a medical condition of a person, predicting prognosis of a medical condition, and predicting genetic mutations of a target tissue, comprising:

receiving a plurality of images of at least one slide depicting at least a portion of the target tissue of the person depicting the medical condition stained with a plurality of stains indicative of respective biomarkers;

creating a plurality of segmentations, by segmenting for each of the plurality of images, into a plurality of cell type segmentations, and a plurality of region type segmentations that include tissue level segmentations;

extracting, for each of the cell type segmentations, a plurality of cell phenotype features from an analysis of the plurality of stains;

assigning, to at least one of: each respective cell type segmentation, a feature vector including the cell phenotype features extracted for the respective segmentation, and an indication of a location of the cell type segmentation relative to one or more region type segmentations that include tissue level segmentations;

creating a cell-graph based on the feature vectors of the plurality of cell type segmentations, wherein each node of the graph denotes a respective cell type segmentation, each node includes associated corresponding feature vector, and edges of the graph represent a physical distance between cell type segmentations corresponding to the respective nodes;

inputting the cell-graph into a graph neural network trained on a training dataset including, for each of a plurality of sample individuals, a plurality of graphs, an indication of a therapy administered to the respective sample individual and at least one of: a clinical outcome of the respective subject individual treated with the therapy, a prognosis for the respective subject, an indication of at least one certain genetic mutation of the target tissue of the respective subject; and obtaining at least one of: an indication of a target therapy likely to be effective for treatment of medical condition in the subject as an outcome of the graph neural network, predicted clinical outcome for the subject having the medical condition, and likelihood of at least one certain genetic mutation of the target tissue.

* * * * *